United States Patent [19]

Daugan

[11] Patent Number: 6,127,542

[45] Date of Patent: Oct. 3, 2000

[54] TETRACYCLIC DERIVATIVES, PROCESS OF PREPARATION AND USE

[75] Inventor: Alain Claude-Marie Daugan, Les Ulis, France

[73] Assignee: ICOS Corporation, Bothell, Wash.

[21] Appl. No.: 09/399,667

[22] Filed: Sep. 21, 1999

Related U.S. Application Data

[60] Continuation of application No. 09/133,078, Aug. 12, 1998, Pat. No. 6,025,494, which is a division of application No. 08/669,389, Jul. 16, 1996, Pat. No. 5,859,006.

[30] Foreign Application Priority Data

Jan. 21, 1994 [GB] United Kingdom .................... 9401090

[51] Int. Cl.$^7$ ...................... C07D 471/00; C07D 491/00; C07D 209/04

[52] U.S. Cl. .................. 546/64; 546/84; 546/85; 548/469

[58] Field of Search .................. 546/64, 84, 85; 548/469

[56] References Cited

U.S. PATENT DOCUMENTS

| | | | |
|---|---|---|---|
| 3,644,384 | 2/1972 | Schulenberg | 260/295 |
| 3,717,638 | 2/1973 | Schulenberg | 260/268 |
| 3,917,599 | 11/1975 | Saxena et al. | 260/268 |

FOREIGN PATENT DOCUMENTS

| | | |
|---|---|---|
| 0 357 122A | 3/1990 | European Pat. Off. |
| 0 362 555A | 4/1990 | European Pat. Off. |
| 1454171 | 10/1976 | United Kingdom . |

OTHER PUBLICATIONS

Saxena et al., *Journal of Medicinal Chemistry*, 16(5), 560–564, 1973.

Ishida et al., *Chem. Pharm. Bull.*, 33(8), 3237–3249, 1985.

DelLouve–Courillon et al., *Tetrahedron*, 46(9), 3245–66, 1990.

Brana et al., *Synth. Comm.*, 201(12), 1793–1820, 1990.

*Primary Examiner*—Richard L. Raymond
*Assistant Examiner*—Tamthom N. Truong
*Attorney, Agent, or Firm*—Marshall, O'Toole, Gerstein, Murray & Borun

[57] ABSTRACT

A compound of formula (I)

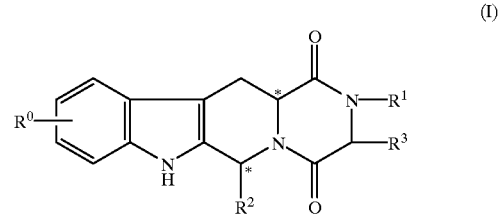

(I)

and salts and solvates thereof, in which:

$R^0$ represents hydrogen, halogen or $C_{1-6}$ alkyl;

$R^1$ represents hydrogen, $C_{1-6}$alkyl, $C_{2-6}$ alkenyl, $C_{2-6}$ alkynyl, halo$C_{1-6}$alkyl, $C_{3-8}$cyloalkyl, $C_{3-8}$cycloalkyl$C_{1-3}$alkyl, aryl$C_{1-3}$alkyl or heteroaryl$C_{1-3}$alkyl;

$R^2$ represents an optionally substituted monocyclic aromatic ring selected from benzene, thiophene, furan and pyridine or an optionally substituted bicyclic ring

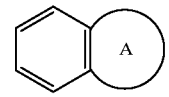

attached to the rest of the molecule via one of the benzene ring carbon atoms and wherein the fused ring A is a 5- or 6-membered ring which may be saturated or partially or fully unsaturated and comprises carbon atoms and optionally one or two heteroatoms selected from oxygen, sulphur and nitrogen; and $R^3$ represents hydrogen or $C_{1-3}$ alkyl, or $R^1$ and $R^3$ together represent a 3- or 4-membered alkyl or alkenyl chain.

A compound of formula (I) is a potent and selective inhibitor of cyclic guanosine 3', 5'-mnonophosphate specific phosphodiesterase (cGMP specific PDE) having a utility in a variety of therapeutic areas where such inhibition is beneficial, including the treatment of cardiovascular disorders.

2 Claims, No Drawings

TETRACYCLIC DERIVATIVES, PROCESS OF PREPARATION AND USE

CROSS-REFERENCE TO RELATED APPLICATION

This application is a continuation of copending application Ser. No. 09/133,078, filed on Aug. 12, 1998, now U.S. Pat. No. 6,025,494, which is a divisional of application Ser. No. 08/669,389, filed on Jul. 16, 1996, now U.S. Pat. No. 5,859,006.

This invention relates to a series of tetracyclic derivatives, to processes for their preparation, pharmaceutical compositions containing them, and their use as therapeutic agents. In particular, the invention relates to tetracyclic derivatives which are potent and selective inhibitors of cyclic guanosine 3′,5′-monophosphate specific phosphodiesterase (cGMP specific PDE) having utility in a variety of therapeutic areas where such inhibition is thought to be beneficial, including the treatment of cardiovascular disorders.

Thus, according to a first aspect, the present invention provides compounds of formula (I)

(I)

and salts and solvates (e.g. hydrates) thereof, in which:

$R^0$ represents hydrogen, halogen or $C_{1-6}$ alkyl;

$R^1$ represents hydrogen, $C_{1-6}$alkyl, $C_{2-6}$ alkenyl, $C_{2-6}$alkynyl, halo$C_{1-6}$alkyl, $C_{3-8}$cycloalkyl, $C_{3-8}$cycloalkyl$C_{1-3}$alkyl, aryl$C_{1-3}$alkyl or heteroaryl$C_{1-3}$alkyl;

$R^2$ represents an optionally substituted monocyclic aromatic ring selected from benzene, thiophene, furan and pyridine or an optionally substituted bicyclic ring attached to the rest of the molecule via one of the benzene ring carbon atoms and wherein the fused ring A is a 5- or 6-membered ring which may be saturated or partially or fully unsaturated and comprises carbon atoms and optionally one or two heteroatoms selected from oxygen, sulphur and nitrogen; and $R^3$ represents hydrogen or $C_{1-3}$ alkyl, or $R^1$ and $R^3$ together represent a 3- or 4-membered alkyl or alkenyl chain.

There is further provided by the present invention a subgroup of compounds of formula (I), the subgroup comprising compounds of formula (Ia)

(Ia)

and salts and solvates (e.g. hydrates) thereof, in which:

$R^0$ represents hydrogen, halogen or $C_{1-6}$ alkyl;

$R^1$ represents hydrogen, $C_{1-6}$alkyl, halo$C_{1-6}$alkyl, $C_{3-8}$cycloalkyl, $C_{3-8}$cycloalkyl$C_{1-3}$alkyl, aryl$C_{1-3}$alkyl or heteroaryl$C_{1-3}$alkyl; and $R^2$ represents an optionally substituted monocyclic aromatic ring selected from benzene, thiophene, furan and pyridine or an optionally substituted bicyclic ring attached to the rest of the molecule via one of the benzene ring carbon atoms and wherein the fused ring A is a 5- or 6-membered ring to which may be saturated or partially or fully unsaturated and comprises carbon atoms and optionally one or two heteroatoms selected from oxygen, sulphur and nitrogen.

Within $R^1$ above, the term "aryl" as part of an aryl$C_{1-3}$ alkyl group means phenyl or phenyl substituted by one or more (e.g. 1, 2 or 3) substituents selected from halogen, $C_{1-6}$alkyl, $C_{1-6}$alkoxy and methylenedioxy. The term "heteroaryl" as part of a heteroaryl$C_{1-3}$alkyl group means thienyl, furyl or pyridyl each optionally substituted by one or more (e.g. 1, 2 or 3) substituents selected from halogen, $C_{1-6}$ alkyl and $C_{1-6}$alkoxy. The term "$C_{3-8}$cycloalkyl" as a group or part of a $C_{3-8}$cycloalkyl$C_{1-3}$alkyl group means a monocyclic ring comprising three to eight carbon atoms. Examples of suitable cycloalkyl rings include the C3-6cycloalkyl rings cyclopropyl, cyclobutyl, cyclopentyl and cyclohexyl.

Within $R^2$ above, optional benzene ring substituents are selected from one or more (e.g. 1, 2 or 3) atoms or groups comprising halogen, hydroxy, $C_{1-6}$alkyl, $C_{1-6}$alkoxy, —$CO_2R^b$, halo$C_{1-6}$alkyl, halo$C_{1-6}$alkoxy, cyano, nitro and $NR^aR^b$, where $R^a$ and $R^b$ are each hydrogen or $C_{1-6}$alkyl, or $R^a$ may also represent $C_{2-7}$alkanoyl or $C_{1-6}$alkylsulphonyl. Optional substituents for the remaining ring systems are selected from one or more (e.g. 1, 2 or 3) atoms or groups comprising halogen, $C_{1-6}$alkyl, $C_{1-6}$alkoxy and aryl$C_{1-3}$alkyl as defined above.

The bicyclic ring may, for example, represent naphthalene, a heterocycle such as benzoxazole, benzothiazole, benzisoxazole, benzimidazole, quinoline, indole, benzothiophene or benzofuran or

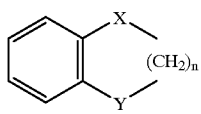

(where n is an integer 1 or 2 and X and Y may each represent CH₂, O, S or NH).

In the above definitions, the term "alkyl" as a group or part of a group means a straight chain or, where available, a branched chain alkyl moiety. For example, it may represent a $C_{1-4}$alkyl function as represented by methyl, ethyl, n-propyl, i-propyl, n-butyl, s-butyl and t-butyl. The term 'alkenyl' as used herein includes straight-chained and branched alkenyl groups, such as vinyl and allyl groups. The term 'alkynyl' as used herein includes straight-chained and branched alkynyl groups, suitably acetylene. The term "halogen" herein means a fluorine, chlorine, bromine or iodine atom. The term "halo$C_{1-6}$alkyl" means an alkyl group as defined above comprising one to six carbon atoms substituted at one or more carbon atoms by one or more (e.g. 1, 2 or 3) halogen atoms. Similarly, a halo$C_{1-6}$alkoxy group is a halo$C_{1-6}$alkyl group as defined above linked to the $R^2$ benzene ring via an oxygen atom. Examples of halo$C_{1-6}$alkyl groups include trifluoromethyl and 2,2,2-trifluoroethyl. An example of a halo$C_{1-6}$alkoxy group is trifluoromethoxy. The term "$C_{2-7}$alkanoyl" means a $C_{1-6}$alkylcarbonyl group where the $C_{1-6}$alkyl portion is as defined above. An example of a suitable $C_{2-7}$alkanoyl group is the $C_2$alkanoyl group acetyl.

It will be appreciated that when $R^0$ is a halogen atom or a $C_{1-6}$alkyl group this substituent may be sited at any available position on the phenyl portion of the tetracyclic ring. However, a particular site of attachment is the ring 10-position.

The compounds of formula (I) may contain two or more asymmetric centres and thus can exist as enantiomers or diastereoisomers. In particular, in formula (I) above two ring chiral centres are denoted with asterisks. It is to be understood that the invention includes both mixtures and separate individual isomers of the compounds of formula (I).

The compounds of formula (I) may also exist in tautomeric forms and the invention includes both mixtures and separate individual tautomers thereof.

The pharmaceutically acceptable salts of the compounds of formula (I) which contain a basic centre are acid addition salts formed with pharmaceutically acceptable acids. Examples include the hydrochloride, hydrobromide, sulphate or bisulphate, phosphate or hydrogen phosphate, acetate, benzoate, succinate, fumarate, maleate, lactate, citrate, tartrate, gluconate, methanesulphonate, benzenesulphonate and p-toluenesulphonate salts. Compounds of the formula (I) can also provide pharmaceutically acceptable metal salts, in particular alkali metal salts, with bases. Examples include the sodium and potassium salts.

A particular group of compounds of the invention are those compounds of formula (I) in which $R^0$ is hydrogen or halogen (e.g. fluorine), especially hydrogen.

Another particular group of compounds of the invention are those compounds of formula (I) in which $R^1$ represents hydrogen, $C_{1-4}$alkyl, halo$C_{1-4}$alkyl, $C_{3-6}$cycloalkyl, $C_{3-6}$cycloalkylmethyl, pyridyl$C_{1-3}$alkyl, furyl$C_{1-3}$alkyl or optionally substituted benzyl. Within this particular group of compounds, examples of $C_{1-4}$alkyl groups are methyl, ethyl, n-propyl, i-propyl and n-butyl. Examples of $C_{3-6}$cycloalkylmethyl groups are cyclopropylmethyl and cyclohexylmethyl. Examples of optionally substituted, benzyl groups include benzyl and halobenzyl (e.g. fluorobenzyl).

A further particular group of compounds of the invention are those compounds of formula (I) in which $R^2$ represents an optionally substituted benzene, thiophene, furan, pyridine or naphthalene ring or an optionally substituted bicyclic ring

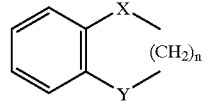

(where n is 1 or 2 and X and Y are each CH₂ or O). Within this particular group of compounds, examples of substituted benzene groups are benzene substituted by one of halogen (e.g. chlorine), hydroxy, $C_{1-3}$alkyl (e.g. methyl, ethyl or i-propyl), $C_{1-3}$alkoxy (e.g. methoxy or ethoxy), —$CO_2R^b$, halomethyl (e.g. trifluoromethyl), halomethoxy (e.g. trifluoromethoxy), cyano, nitro or $NR^aR^b$ where $R^a$ and $R^b$ are each hydrogen or methyl or $R^a$ is acetyl; or benzene substituted by dihalo (e.g. dichloro) or by $C_{1-3}$alkoxy (e.g. methoxy) and one of halogen (e.g. chlorine) and hydroxy. An example of a substituted thiophene ring is a halo (e.g. bromo) substituent thiophene ring.

A still further particular group of compounds of formula I are those wherein $R^3$ represents hydrogen or $R^1$ and $R^3$ together represent a 3-membered alkyl chain.

A preferred group of compounds of the invention are the cis isomers of formula (I) represented by formula (Ib)

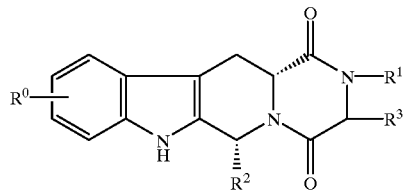

(Ib)

and mixtures thereof with their cis optical enantiomers, including racemic mixtures, and salts and solvates (e.g. hydrates) of these compounds in which $R^0$ is hydrogen or halogen (e.g. fluorine), especially hydrogen and $R^1$, $R^2$ and $R^3$ are as defined previously.

The single isomers represented by formula (Ib), i.e. the 6R, 12aR isomers, are particularly preferred.

Within the above definitions $R^1$ may preferably represent $C_{1-4}$alkyl (e.g. methyl, ethyl, i-propyl and n-butyl), $C_{3-6}$cycloalkyl (e.g. cyclopentyl) or $C_{3-6}$cycloalkylmethyl (e.g. cyclopropylmethyl).

$R^2$ may preferably represent a substituted benzene ring such as benzene substituted by $C_{1-3}$alkoxy (e.g. methoxy) or by $C_{1-3}$alkoxy (e.g. methoxy) and halogen (e.g. chlorine), particularly 4-methoxyphenyl or 3-chloro-4-methoxyphenyl, or $R^2$ may preferably represent 3,4-methylenedioxyphenyl.

It is to be understood that the present invention covers all appropriate combinations of particular and preferred groupings hereinabove.

Particular individual compounds of the invention include:
Cis-2,3,6,7,12,12a-hexahydro-2-(4-pyridylmethyl)-6-(3, 4-methylenedioxyphenyl)-pyrazino[2',1':6,1]pyrido[3, 4b]indole-1,4dione;
Cis-2,3,6,7,12,12a-hexahydro-6-(2,3-dihydrobenzo[b] furan-5-yl)-2-methyl-pyrazino[2',1':6,1]pyrido[3,4b] indole-1,4-dione;
Cis-2,3,6,7,12,12a-hexahydro-6-(5-bromo-2-thienyl)-2-methyl-pyrazino[2',1':6,1]pyrido[3,4-b]indole-1,4-dione;

Cis-2,3,6,7,12,12a-hexahydro-2-butyl-6-(4-methylphenyl)-pyrazino[2',1':6,1]pyrido[3,4b]indole-1,4-dione;

(6R,12aR)-2,3,6,7,12,12a-Hexahydro-2-isopropyl-6-(3,4-methylenedioxyphenyl)-pyrazino[2',1':6,1]pyrido[3,4-b]indole-1,4-dione;

(6R,12aR)-2,3,6,7,12,12a-Hexahydro-2-cyclopentyl-6-(3,4-methylenedioxyphenyl)-pyrazino[2',1':6,1]pyrido[3,4b]indole-1,4-dione;

(6R,12aR)-2,3,6,7,12,12a-Hexahydro-2-cyclopropylmethyl-6-(4-methoxyphenyl)-pyrazino[2',1':6,1]pyrido[3,4b]indole-1,4-dione;

(6R,12aR)-2,3,6,7,12,12a-Hexahydro-6-(3-chloro-4-methoxyphenyl)-2-methyl-pyrazino[2',1':6,1]pyrido[3,4-b]indole-1,4-dione;

(6R,12aR)-2,3,6,7,12,12a-Hexahydro-2-methyl6-(3,4-methylenedioxyphenyl)-pyrazino[2',1':6,1]pyrido[3,4-b]indole-1,4-dione;

(6R,12aR)-2,3,6,7,12,12a-Hexahydro-6-(3,4-methylenedioxyphenyl)-pyrazino[2',1':6,1]pyrido[3,4-b]indole-1,4-dione;

(5aR,12R, 14aS)-1,2,3,5,6,11,12,14a-Octahydro-12-(3,4-methylenedioxyphenyl)-pyrrolo[1",2":4',5']pyrazino[2',1':6,1]pyrido[3,4-b]indole-5-1,4-dione;

and physiologically acceptable salts and solvates (e.g. hydrates) thereof.

A specific compound of the invention is:

(6R, 12aR)-2,3,6,7,12,12a-hexahydro-2-methyl-6-(3,4-methylenedioxyphenyl)-pyrazino[2',1':6,1]pyrido[3,4-b]indole-1,4-dione;

and physiologically acceptable salts and solvates (e.g. hydrates) thereof.

It has been shown that compounds of the present invention are potent and selective inhibitors of cGMP specific PDE. Thus, compounds of formula (I) are of interest for use in therapy, specifically for the treatment of a variety of conditions where inhibition of cGMP specific PDE is thought to be beneficial.

As a consequence of the selective PDE V inhibition exhibited by compounds of the present invention, cGMP levels are elevated, which in turn can give rise to beneficial anti-platelet, anti-neutrophil, anti-vasospastic, vasodilatory, natriuretic and diuretic activities as well as potentiation of the effects of endothelium-derived relaxing factor (EDRF), nitrovasodilators, atrial natriuretic factor (ANF), brain natriuretic peptide (BNP), C-type natriuretic peptide (CNP) and endothelium-dependent relaxing agents such as bradykinin, acetylcholine and 5-HT$_1$. The compounds of formula (I) therefore have utility in the treatment of a number of disorders, including stable, unstable and variant (Prinzmetal) angina, hypertension, pulmonary hypertension, congestive heart failure, renal failure, atherosclerosis, conditions of reduced blood vessel patency (e.g. post-percutaneous transluminal coronary angioplasty), peripheral vascular disease, vascular disorders such as Raynaud's disease, inflammatory diseases, stroke, bronchitis, chronic asthma, allergic asthma, allergic rhinitis, glaucoma and diseases characterised by disorders of gut motility (e.g. irritable bowel syndrome).

It will be appreciated that references herein to treatment extend to prophylaxis as well as treatment of established conditions.

It will also be appreciated that a compound of formula (I), or a physiologically acceptable salt or solvate thereof can be administered as the raw compound, or as a pharmaceutical composition containing either entity.

There is thus provided as a further aspect of the invention a compound of formula (I) for use in the treatment of stable, unstable and variant (Prinzmetal) angina, hypertension, pulmonary hypertension, chronic obstructive pulmonary disease, congestive heart failure, renal failure, atherosclerosis, conditions of reduced blood vessel patency, (e.g. post-PTCA), peripheral vascular disease, vascular disorders such as Raynaud's disease, inflammatory diseases, stroke, bronchitis, chronic asthma, allergic asthma, allergic rhinitis, glaucoma or diseases characterised by disorders of gut motility (e.g. IBS).

According to another aspect of the invention, there is provided the use of a compound of formula (I) for the manufacture of a medicament for the treatment of stable, unstable and variant (Prinzmetal) angina, hypertension, pulmonary hypertension, chronic obstructive pulmonary disease, congestive heart failure, renal failure, atherosclerosis, conditions of reduced blood vessel patency, (e.g. post-PTCA), peripheral vascular disease, vascular disorders such as Raynaud's disease, inflammatory diseases, stroke, bronchitis, chronic asthma, allergic asthma, allergic rhinitis, glaucoma or diseases characterised by disorders of gut motility (e.g. IBS).

In a further aspect, the invention provides a method of treating stable, unstable and variant (Prinzmetal) angina, hypertension, pulmonary hypertension, chronic obstructive pulmonary disease, congestive heart failure, renal failure, atherosclerosis, conditions of reduced blood vessel patency, (e.g. post-PTCA), peripheral vascular disease, vascular disorders such as Raynaud's disease, inflammatory diseases, stroke, bronchitis, chronic asthma, allergic asthma, allergic rhinitis, glaucoma or diseases characterised by disorders of gut motility (e.g. IBS) in a human or non-human animal body which comprises administering to said body a therapeutically effective amount of a compound with formula (I).

Compounds of the invention may be administered by any suitable route, for example by oral, buccal, sub-lingual, rectal, vaginal, nasal, topical or parenteral (including intravenous, intramuscular, subcutaneous and intracoronary) administration. Oral administration is generally preferred.

For administration to man in the curative or prophylactic treatment of the disorders identified above, oral dosages of a compound of formula (I) will generally be in the range of from 0.5–800 mg daily for an average adult patient (70 kg). Thus for a typical adult patient, individual tablets or capsules contain from 0.2–400 mg of active compound, in a suitable pharmaceutically acceptable vehicle or carrier, for administration in single or multiple doses, once or several times per day. Dosages for intravenous, buccal or sublingual administration will typically be within the range of from 0.1–400 mg per single dose as required. In practice the physician will determine the actual dosing regimen which will be most suitable for an individual patient and it will vary with the age, weight and response of the particular patient. The above dosages are exemplary of the average case but there can be individual instances in which higher or lower dosage ranges may be merited, and such are within the scope of this invention.

For human use, a compound of the formula (I) can be administered alone, but will generally be administered in admixture with a pharmaceutical carrier selected with regard to the intended route of administration and standard pharmaceutical practice. For example, the compound may be administered orally, buccally or sublingually, in the form of tablets containing excipients such as starch or lactose, or in capsules or ovules either alone or in admixture with excipients, or in the form of elixirs or suspensions containing flavouring or colouring agents. Such liquid preparations may be prepared with pharmaceutically acceptable additives such as suspending agents (e.g. methylcellulose, a semi-synthetic glyceride such as witepsol or mixtures of glycerides such as a mixture of apricot kernel oil and PEG6 esters or mixtures of PEG-8 and caprylic/capric glycerides). A compound may also be injected parenterally, for example intravenously, intramuscularly, subcutaneously or intracoronarily. For parenteral administration, the compound is best used in the form of a sterile aqueous solution which may contain other substances, for example salts, or monosaccharides such as mannitol or glucose, to make the solution isotonic with blood.

Thus, the invention provides in a further aspect a pharmaceutical composition comprising a compound of the formula (I) together with a pharmaceutically acceptable diluent or carrier therefor.

There is further provided by the present invention a process of preparing a pharmaceutical composition comprising a compound of formula (I), which process comprises mixing a compound of formula (I) together with a pharmaceutically acceptable diluent or carrier therefor.

A compound of formula (I) may also be used in combination with other therapeutic agents which may be useful in the treatment of the above-mentioned disease states. The invention thus provides, in another aspect, a combination of a compound of formula (I) together with another therapeutically active agent.

The combination referred to above may conveniently be presented for use in the form of a pharmaceutical formulation and thus pharmaceutical compositions comprising a combination as defined above together with a pharmaceutically acceptable diluent or carrier comprise a further aspect of the invention.

The individual components of such a combination may also be administered either sequentially or simultaneously in separate pharmaceutical formulations.

Appropriate doses of known therapeutic agents for use in combination with a compound of formula (I) will be readily appreciated by those skilled in the art.

Compounds of formula (I) may be prepared by any suitable method known in the art or by the following processes which form part of the present invention. In the methods below $R^0$, $R^1$ and $R^2$ are as defined in formula (I) above unless otherwise indicated.

Thus, a process (A) for preparing a compound of formula (I) wherein $R^3$ represents hydrogen comprises treating a compound of formula (II)

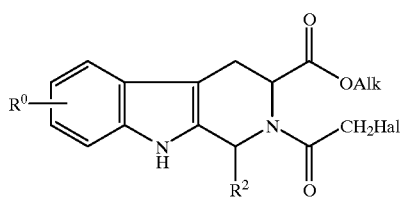

(II)

(in which Alk represents $C_{1-6}$alkyl, e.g. methyl or ethyl and Hal is a halogen atom, e.g. chlorine) with a primary amine $R^1NH_2$ in a suitable solvent such as an alcohol (e.g. methanol or ethanol) or a mixture of solvents, conveniently at a temperature of from 20° C. to reflux (e.g. at about 50° C.).

A compound of formula (II) may conveniently be prepared by treating a compound of formula (III)

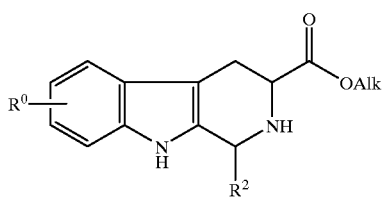

(III)

with a haloacetyl halide (e.g. chloroacetyl chloride) in a suitable solvent such as a halogenated hydrocarbon (e.g. trichloromethane or dichloromethane), or an ether (e.g. tetrahydrofuran), preferably in the presence of a base such as an organic amine (e.g. a trialkylamine such as triethylamine) or an alkali metal carbonate or bicarbonate (e.g. $NaHCO_3$). The reaction may conveniently be effected at a temperature of from $-20°$ C. to $+20°$ C. (e.g. at about 0° C.).

A compound of formula (I) may also be prepared from a compound of formula (III) in a two-step procedure via a compound of formula (II) isolated without purification.

Compounds of formula (I) may be prepared as individual enantiomers in two steps from the appropriate enantiomer of formula (III) or as mixtures (e.g. racemates) of either pairs of cis or trans isomers from the corresponding mixtures of either pairs of cis or trans isomers of formula (III).

Individual enantiomers of the compounds of the invention may be prepared from racemates by resolution using methods known in the art for the separation of racemic mixtures into their constituent enantiomers, for example using HPLC (high performance liquid chromatography) on a chiral column such as Hypersil naphthylurea.

A compound of formula (III) may conveniently be prepared from a tryptophan alkyl ester of formula (IV)

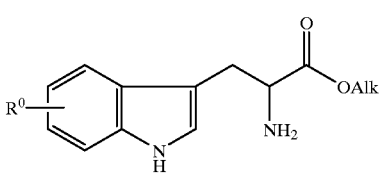

(IV)

(where Alk is as previously defined) or a salt thereof (e.g. the hydrochloride salt) according to either of the following procedures (a) and (b). Procedure (b) is only suitable for preparing cis isomers of formula (III) and may be particularly suitable for preparing individual cis enantiomers of formula (III) from D- or L-tryptophan alkyl esters as appropriate.

Procedure (a)

This comprises a Pictet-Spengler cyclisation between a compound of formula (IV) and an aldehyde $R^2CHO$. The reaction may conveniently be effected in a suitable solvent such as a halogenated hydrocarbon (e.g. dichloromethane) or an aromatic hydrocarbon (e.g. toluene) in the presence of an acid such as trifluoroacetic acid. The reaction may conveniently be carried out at a temperature of from $-20°$ C. to reflux to provide a compound of formula (III) in one a step. The reaction may also be carried out in a solvent such as an aromatic hydrocarbon (e.g. benzene or toluene) under reflux, optionally using a Dean-Stark apparatus to trap the water produced.

The reaction provides a mixture of cis and trans isomers which may be either individual enantiomers or racemates of pairs of cis or trans isomers depending upon whether racemic or enantiomerically pure tryptophan alkyl ester was used as the starting material. Individual cis or trans enantiomers may conveniently be separated from mixtures thereof by fractional crystallisation or by chromatography (e.g. flash column chromatography) using appropriate solvents and eluents. Similarly, pairs of cis and trans isomers may be separated by chromatography (e.g. flash column chromatography) using appropriate eluents. An optically pure trans isomer may also be converted to an optically pure cis isomer using suitable epimerisation procedures. One such procedure comprises treating the trans isomer or a mixture (e.g. 1:1 mixture) of cis and trans isomers with methanolic or aqueous hydrogen chloride at a temperature of from 0° C. to the refluxing temperature of the solution. The mixture may then be subjected to chromatography (e.g. flash column chromatography) to separate the resulting diastereoisomers, or in the procedure utilising aqueous hydrogen chloride the desired cis isomer precipitates out as the hydrochloride salt which may then be isolated by filtration.

Procedure (b)

This comprises a four-step procedure from a compound of formula (IV) or a salt thereof (e.g. the hydrochloride salt). The procedure is particularly suitable for preparing a 1R, 3R isomer of formula (III) from a D-tryptophan alkyl ester of formula (IV) or a salt thereof (e.g. the hydrochloride salt). Thus, a first step (i) comprises treating a compound of formula (IV) with an acid halide $R^2COHal$ (where Hal is as previously defined) in the presence of a base, e.g. an organic base such as a trialkylamine (for example triethylamine), to provide a compound of formula (V)

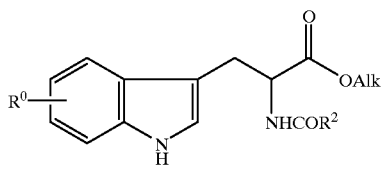

(V)

The reaction may be conveniently carried out in a suitable solvent such as a halogenated hydrocarbon (e.g. dichloromethane) or an ether (e.g. tetrahydrofuran) and at a temperature of from −20° C. to +40° C.

Step (ii) comprises treating a compound of formula (V) with an agent to convert the amide group to a thioamide group. Suitable sulfurating agents are well-known in the art. Thus, for example, the reaction may conveniently be effected by treating (V) with Lawesson's reagent. This reaction may conveniently be carried out in a suitable solvent such as an ether (e.g. dimethoxyethane) or an aromatic hydrocarbon (e.g. toluene) at an elevated temperature such as from 40° C. to 80° C. to provide a compound of formula (VI)

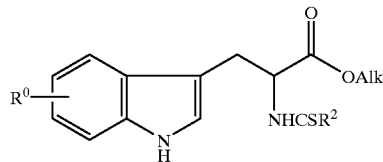

(VI)

Step (iii) comprises treating a compound of formula (VI) with a suitable agent to provide a compound of formula (VII)

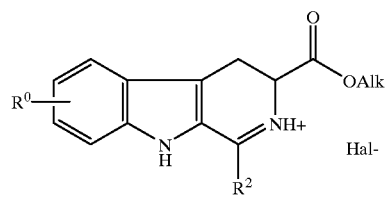

(VII)

(where Hal is a halogen atom, e.g. iodine). The reaction may conveniently be effected by treating (VI) with an alkylating agent such as a methyl halide (e.g. methyl iodide) or an acylating agent such as an acetyl halide (e.g. acetyl chloride) in a suitable solvent such as a halogenated hydrocarbon (e.g. dichloromethane) at an elevated temperature (e.g. under reflux).

In step (iv) the resulting iminium halide of formula (VII) may be treated with a reducing agent such as boron hydride, e.g. sodium borohydride, to provide the desired compound of formula (III). The reduction may conveniently be effected at a low temperature, e.g. within the range of −100° C. to 0° C., in a suitable solvent such as an alcohol (e.g. methanol).

There is further provided by the present invention a process (B) for preparing a compound of formula (I), wherein $R^1$ and $R^3$ together represent a 3- or 4-membered alkyl or alkenyl chain, which process (B) comprises cyclisation of a compound of formula (VIII)

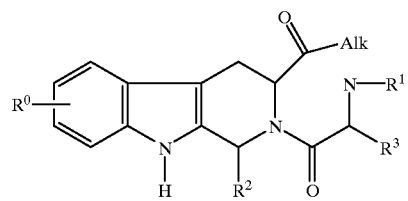

(VIII)

wherein Alk represents $C_{1-6}$alkyl and $R^1$ and $R^3$ together represent a 3- or 4-membered chain both as hereinbefore described. The cyclisation is suitably carried out in an organic solvent or solvents, such as an alcoholic solvent (e.g. methanol) and optionally an ether solvent such as tetrahydrofuran, and in the presence of a reducing agent, aptly a palladium catalyst, such as palladium on carbon.

Conveniently a compound of formula (VII) is prepared by reaction of a compound of formula (III) as hereinbefore described with a compound of formula (IX)

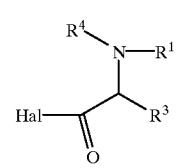

(IX)

wherein Hal represents a halogen atom as hereinbefore described, $R^1$ and $R^3$ together represent a 3- or 4-membered chain as hereinbefore described and $R^4$ represents a protecting group, suitably a benzyloxycarbonyl group or the like. Typically the reaction is carried out in a chlorinated organic solvent, such as dichloromethane, and a tertiary amine, such as triethylamine or the like.

According to a further aspect of the present invention, there is provided a process (C) for preparing a compound of formula (I) wherein $R^3$ represents $C_{1-3}$alkyl, which process comprises cyclisation of a compound of formula (X)

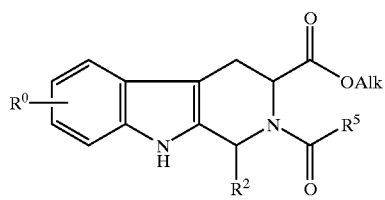

(X)

wherein Alk represents $C_{1-6}$alkyl as hereinbefore described and $R^5$ represents $C_{2-5}$alkyl, substituted at $C_1$ by a halogen atom, the halogen atom being as hereinbefore described. Suitably the cyclisation is achieved by reflux for many hours, such as 22 to 26 hours, in the presence of an ether solvent, such as tetrahydrofuran, and a suitable amine as hereinafter described in the accompanying examples.

Aptly a compound of formula (X) can be prepared from a compound of formula (III) by suitable acylation techniques, such as reaction with a $C_{3-6}$carboxylic acid, substituted at $C_2$ by a halogen atom in a halogenated organic solvent, such as dichloromethane.

Compounds of formula (I) may be converted to other compounds of formula (I). Thus, for example, when $R^2$ is a substituted benzene ring it may be necessary or desirable to prepare the suitably substituted compound of formula (I) subsequent to process (A), (B) or (C) as above. Examples of appropriate interconversions include nitro to amino or aralkyloxy to hydroxy by suitable reducing means (e.g. using a reducing agent such as $SnCl_2$ or a palladium catalyst, such as palladium-on-carbon), or amino to substituted amino such as acylamino or sulphonylamino using standard acylating or sulphonylating conditions. In the case where $R^2$ represents a substituted bicyclic system, suitable interconversion can involve removal of a substituent, such as by treatment with a palladium catalyst (e.g. palladium-on-carbon) whereby, for example, a benzyl substituent may be removed from a suitable bicyclic system.

The pharmaceutically acceptable acid addition salts of the compounds of formula (I) which contain a basic centre may be prepared in a conventional manner. For example, a solution of the free base may be treated with a suitable acid, either neat or in a suitable solution, and the resulting salt isolated either by filtration or by evaporation under vacuum of the reaction solvent. Pharmaceutically acceptable base addition salts may be obtained in an analogous manner by treating a solution of a compound of formula (I) with a suitable base. Both types of salt may be formed or interconverted using ion-exchange resin techniques.

Compounds of the invention may be isolated in association with solvent molecules by crystallisation from or evaporation of an appropriate solvent.

Thus, according to a further aspect of the invention, we provide a process for preparing a compound of formula (I) or a salt or solvate (e.g. hydrate) thereof which comprises process (A), (B) or (C) as hereinbefore described followed by i) an interconversion step; and/or either ii) salt formation; or iii) solvate (e.g. hydrate) formation.

There is further provided by the present invention compounds of formulae (II), (VIII), (X) and further compounds of formulae (III), (V), (VI) and (VII), with the exception for compounds (III), (V), (VI) and (VII) wherein $R^0$ is hydrogen, $R^2$ is phenyl and Alk is methyl.

The synthesis of the compounds of the invention and of the intermediates for use therein are illustrated by the following, non-limiting Examples. In the Examples section hereinafter the following abbreviations are used:

DMSO (dimethylsulphoxide), MeOH (methanol), EtOH (ethanol), DMF (dimethylformamide), EtOAc (ethyl acetate) and THF (tetrahydrofuran).

Intermediates 1 and 2

Methyl 1,2,3,4-tetrahydro-1-(3,4-methylenedioxyphenyl)-9H-pyrido[3,4-b]indole-3-carboxylate, cis and trans isomers To a stirred solution of racemic tryptophan methyl ester (13 g) and piperonal (9.7 g) in anhydrous $CH_2Cl_2$ (300 mL) cooled at 0° C. was added dropwise trifluoroacetic acid (9 mL) and the solution was allowed to react at ambient temperature. After 4 days, the yellow solution was diluted with $CH_2Cl_2$ (100 mL), washed with a saturated aqueous solution of $NaHCO_3$, then with water and dried over $Na_2SO_4$. The organic layer was evaporated to dryness under reduced pressure and the residue was purified by flash chromatography eluting with $CH_2Cl_2$/MeOH (99/1) to give first Intermediate 1, the cis isomer (6.5 g) m.p.: 90–93° C. followed by Intermediate 2, the trans isomer (6.4 g) m.p.: 170° C.

The following compounds were obtained in a similar manner:

Intermediates 3 and 4

Methyl 1,2,3,4-tetrahydro-1-(4-methoxyphenyl)-9H-pyrido[3,4-b]indole-3-carboxylate, cis and trans isomers The same method but starting from racemic tryptophan methyl ester and 4-methoxybenzaldehyde gave Intermediate 3, the cis isomer as white crystals m.p.: 142° C. and Intermediate 4, the trans isomer as white crystals m.p.: 209–210° C.

Intermediate 5

Methyl 1,2,3,4-tetrahydro-1-3-methoxyphenyl)-9H-pyrido[3,4-b]indole-3-carboxylate, cis isomer The same method but starting from racemic tryptophan methyl ester and 3-methoxybenzaldehyde gave the title compound as white crystals m.p.: 146° C.

Intermediates 6 and 7

Methyl 1,2,3,4-tetrahydro-1-(4-ethoxyphenyl)-9H-pyrido[3,4-b]indole-3-carboxylate, cis and trans isomers The same method but starting from racemic tryptophan methyl ester and 4-ethoxybenzaldehyde gave Intermediate 6, the cis isomer as white crystals m.p.: 180° C. and Intermediate 7, the trans isomer as white crystals m.p.: 196–198° C.

Intermediates 8 and 9

Methyl 1,2,3,4-tetrahydro-1-2,3-dihydrobenzo[b] furan-5-yl)-9H-pyrido[3,4-b]indole-3-carboxylate, cis and trans isomers The same method but starting from racemic tryptophan methyl ester and 2,3-dihydrobenzo[b]furan-5- carboxaldehyde gave Intermediate 8, the cis isomer as white crystals m.p.: 106–109° C. and Intermediate 9, the trans isomer as white crystals m.p.: 219–222° C.

Intermediates 10 and 11

Methyl 1,2,3,4-tetrahydro-1-(3,4-ethylenedioxyphenyl)-9H-pyrido[3,4-b]indole-3-carboxylate, cis and trans isomers The same method but starting from racemic tryptophan methyl ester and 1,4-benzodioxan-6-carboxaldehyde gave Intermediate 10, the cis isomer as white crystals m.p.: 104–106° C. and Intermediate 11, the trans isomer as white crystals m.p.: 207–209° C.

Intermediate 12

Methyl 1,2,3,4-tetrahydro-1-(2-chlorophenyl)-9H-pyrido[3,4-b]indole-3-carboxylate, mixture of cis and trans isomers The same method but starting from racemic tryptophan methyl ester and 2-chlorobenzaldehyde gave the title compound as white crystals m.p.: 154° C.

Intermediates 13 and 14

Methyl 1,2,3,4-tetrahydro-1-(4-chlorophenyl)-9H-pyrido[3,4-b]indole-3-carboxylate, cis and trans isomers The same method but starting from racemic tryptophan methyl ester and 4-chlorobenzaldehyde gave Intermediate 13, the cis isomer as white crystals m.p. 208–209° C. and Intermediate 14, the trans isomer as white crystals m.p.: 108–109° C.

Intermediates 15 and 16

Methyl 1,2,3,4-tetrahydro-1-(3,4-dichlorophenyl)-9H-pyrido[3,4-b]indole-3-carboxylate, cis and trans isomers The same method but starting from racemic tryptophan methyl ester and 3,4-dichlorobenzaldehyde gave Intermediate 15, the cis isomer as a white solid $^1$H NMR (CDCl$_3$) δ (ppm): 7.8–7 (m, 8H, H aromatic); 5.15 (brs, 1H, H-1); 3.9–3.8 (dd, 1H, H-3) 3.7 (s, 3H, CO$_2$CH$_3$); 3.2–3.1 (ddd, 1H, H4) 2.9 (m, 1H-4); 2.4 (brs, 1H, NH) and Intermediate 16, the trans isomer as a white solid m.p.: 204° C.

Intermediate 17

Methyl 1,2,3,4-tetrahydro-1-(1,2,3,4-tetrahydro-6-naphthyl)9H-pyrido[3,4-b]indole-3-carboxylate, cis isomer The same method but starting from racemic tryptophan methyl ester and 1,2,3,4-tetrahydronaphthyl-6-carboxaldehyde gave the title compound as a white solid $^1$H NMR (CDCl$_3$) δ (ppm): 7.7–7(m, 8H, H aromatic); 5.2 (s, 1H, H-1); 4.0 (dd, 1H, H-3); 3.8 (s, 3H, CO$_2$CH$_3$); 3.2 (m, 1H, H-4); 3.0 (m, 1H, H-4); 2.7 (m, 4H, CH$_2$Ar); 1.7 (s, 4H, CH$_2$CH$_2$Ar).

Intermediates 18 and 19

Methyl 1,2,3,4-tetrahydro-1-(2-naphthyl)-9H-pyrido[3,4-b]indole-3-carboxylate, cis and trans isomers The same method but starting from racemic tryptophan methyl ester and 2-naphthaldehyde gave Intermediate 18, the cis isomer as a white solid $^1$H NMR (CDCl$_3$) δ (ppm): 8–6.9 (m, 12H, H aromatic); 5.4 (s, 1H, H-1); 3.95 (dd, 1H, H-3); 3.7 (s, 3H, CO$_2$CH$_3$) 3.2 (ddd, 1H, H-4); 3 (m, 1H, H-4); 2.5 (brs, 1H, NH) and Intermediate 19, the trans isomer as a white solid (0.6 g) m.p.: 119° C.

Intermediates 20 and 21

Methyl 1,2,3,4-tetrahydro-1-(2-thienyl)-9H-pyrido[3,4-b]indole-3-carboxylate, cis and trans isomers The same method but starting from racemic tryptophan methyl ester and 2-thiophenecarboxaldehyde gave Intermediate 20, the cis isomer as a pale yellow solid m.p.: 134–137° C. and Intermediate 21, the trans isomer as white crystals m.p.: 169° C.

Intermediates 22 and 23

Ethyl 1,2,3,4-tetrahydro-1-(3-thienyl)-9H-pyrido[3,4-b]indole-3-carboxylate, cis and trans isomers The same method but starting from racemic tryptophan ethyl ester and 3-thiophenecarboxaldehyde gave Intermediate 22, the cis isomer as white crystals m.p.: 130° C. and Intermediate 23, the trans isomer as white crystals m.p.: 182–184° C.

Intermediates 24 and 25

Methyl 1,2,3,4-tetrahydro1-(5-bromo-2-thienyl)-9H-pyrido[3,4-b]indole-3-carboxylate, cis and trans isomers The same method but starting from racemic tryptophan methyl ester and 5-bromo-2-thiophenecarboxaldehyde gave Intermediate 24, the cis isomer as a cream solid m.p.: 130° C. and Intermediate 25, the trans isomer as a cream solid m.p.: 205° C.

Intermediates 26 and 27

Methyl 1,2,3,4-tetrahydro-1-(4-bromo-2-thienyl)-9H-pyrido[3,4-b]indole-3-carboxylate, cis and trans isomers The same method but starting from racemic tryptophan methyl ester and 4-bromo-2-thiophenecarboxaldehyde gave Intermediate 26, the cis isomer as a cream solid m.p.: 200° C. and Intermediate 27, the trans isomer as a cream solid m.p.: 120° C.

Intermediate 28

Methyl 1,2,3,4-tetrahydro-1-(3-furyl)-9H-pyrido[3,4-b]indole-3-carboxylate, mixture of cis and trans isomers The same method but starting from racemic tryptophan methyl ester and 3-furaldehyde gave the title compound as a yellow solid m.p.: 130° C.

Intermediates 29 and 30

Ethyl 1,2,3,4-tetrahydro-1-(5-methyl-2-furyl)-9H-pyrido[3,4-b]indole-3-carboxylate, cis and trans isomers The same method but starting from racemic tryptophan ethyl ester and 5-methylfurfural gave Intermediate 29, the cis isomer as a oily compound $^1$H NMR (CDCl$_3$) δ (ppm):

7.7 (brs, 1H, NH indole); 7.5 (d, 1H, H aromatic); 7.25–6.9 (m, 3H, H aromatic); 6.15 (d, 1H, H aromatic); 5.85 (m, 1H, H aromatic); 5.25 (brs, 1H, H-1); 4.2 (q, 2H, $CO_2CH_2CH_3$); 3.8 (dd, 1H, H-3); 3.2–2.8 (m, 2H, H-4); 2.2 (s, 3H, $CH_3$); 1.25 (t, 3H, $CO_2CH_2CH_3$) and Intermediate 30, the trans isomer as a cream solid m.p.: 152° C.

Intermediates 31 and 32

Ethyl 1,2,3,4-tetrahydro-1-(4-methylphenyl)-9H-pyrido[3,4b]indole-3-carboxylate, cis and trans isomers The same method but starting from racemic tryptophan ethyl ester and p-tolualdehyde gave Intermediate 31, the cis isomer as white crystals m.p.: 148° C. and Intermediate 32, the trans isomer as white crystals m.p.: 180° C.

Intermediates 33 and 34

Methyl 1,2,3,4-tetrahydro-1-(3-methylphenyl)-9H-pyrido[3,4-b]indole-3-carboxylate, cis and trans isomers The same method but starting from racemic tryptophan methyl ester and m-tolualdehyde gave Intermediate 33, the cis isomer as white crystals $^1$H NMR (CDCl$_3$) δ (ppm): 7.6–7 (m, 9H, H aromatic); 5.2 (brs, 1H, H-1); 4–3.9 (dd, 1H, H-3) 3.8 (s, 3H, $CO_2CH_3$); 3.2–3.1 (ddd, 1H, H-4) 3 (m, 1H, H-4); 2.35 (s, 3H, $CH_3$); 1.7 (brs, 1H, NH) and Intermediate 34, the trans isomer as a white solid m.p.: 175° C.

Intermediates 35 and 36

Methyl 1,2,3,4-tetrahydro-1-(4-trifluoromethylphenyl)-9H-pyrido[3,4-b]indole-3-carboxylate, cis and trans isomers The same method but starting from racemic tryptophan methyl ester and 4-trifluoromethylbenzaldehyde gave Intermediate 35, the cis isomer as pale yellow crystals m.p.: 190° C. and Intermediate 36, the trans isomer as pale yellow crystals m.p.: 203° C.

Intermediates 37 and 38

Ethyl 1,2,3,4-tetrahydro-1-(4-cyanophenyl)-9H-pyrido[3,4-b]indole-3-carboxylate, cis and trans isomers The same method but starting from racemic tryptophan ethyl ester and 4-cyanobenzaldehyde gave Intermediate 37, the cis isomer as white crystals m.p.: 200° C. and Intermediate 38, the trans isomer as white crystals m.p.: 156° C.

Intermediate 39

Methyl 1,2,3,4-tetrahydro-1-(4-hydroxyphenyl)-9H-pyrido[3,4-b]indole-3-carboxylate, cis isomer The same method but starting from racemic tryptophan ethyl ester and 4-hydroxybenzaldehyde gave the title compound as pale yellow crystals $^1$H NMR (DMSO) δ (ppm): 10.3 (s, 1H, NH-indole) 9.4 (s, 1H, OH); 7.8–7.5 (m, 8H, H aromatic); 5.1 (brs, 1H, H-1); 3.9 (m, 1H, H-3); 3.75 (s, 3H, $CO_2CH_3$) 3.1 (m, 1H, H-4); 2.8 (m, 1H, H-4).

Intermediate 40

Methyl 1,2,3,4-tetrahydro-1-(3-hydroxy-4-methoxyphenyl)-9H-pyrido[3,4-b]indole-3-carboxylate, cis isomer The same method but starting from racemic tryptophan methyl ester and 3-hydroxy-4-methoxybenzaldehyde gave the title compound as a yellow solid m.p.: 140–148° C.

Intermediate 41

Methyl 1,2,3,4-tetrahydro-1-(4-hydroxy-3-methoxyphenyl)-9H-pyrido[3,4-b]indole-3-carboxylate, cis isomer The same method but starting from racemic tryptophan methyl ester and 4-hydroxy-3-methoxybenzaldehyde gave the title compound as a cream solid m.p.: 195° C.

Intermediate 42

Methyl 1,2,3,4-tetrahydro-1-(4-ethylphenyl)-9H-pyrido[3,4-b]indole-3-carboxylate, cis and trans isomers The same method but starting from racemic tryptophan methyl ester and 4-ethylbenzaldehyde gave the cis and trans isomer of the title compound.

Cis isomer: white solid $^1$H NMR (CDCl$_3$) δ (ppm): 7.65–7.1 (m, 9H, H aromatic); 5.25 (brs, 1H, H-1); 4(dd, 1H, H-3); 3.9 (s, 3H, $CO_2CH_3$); 3.4 (ddd, 1H, H-4); 3.1 (m, 1H, H-4); 2.7 (q, 2H, C$\underline{H}_2$CH$_3$) 1.4 (t, 3H, CH$_2$C$\underline{H}_3$). Trans isomer: white solid m.p.: 187° C.

Intermediates 43 and 44

Methyl 1,2,3,4-tetrahydro-1-(4-isopropylphenyl)-9H-pyrido[3,4-b]indole-3-carboxylate, cis and trans isomers The same method but starting from racemic tryptophan ethyl ester and 4-isopropylbenzaldehyde gave Intermediate 43, the cis isomer as a white solid $^1$H NMR (DMSO) δ (ppm): 10.15 (s, 1H, NH indole); 7.3–6.7 (m, 8H, H aromatic); 5 (brs, 1H, H-1); 3.6 (m, 1H, H-3); 3.5 (s, 3H, $CO_2CH_3$); 2.95–2.5 (m, 3H, H-4+C$\underline{H}$-Me)$_2$) 2.4 (brs, 1H, NH); 1(d, 6H, 2×CH$_3$) and Intermediate 44, the trans isomer as a white solid m.p.: 189° C.

Intermediates 45 and 46

Ethyl 1,2,3,4-tetrahydro-1-(4nitrophenyl)-9H-pyrido[3,4-b]indole-3-carboxylate, cis and trans isomers The same method but starting from racemic tryptophan ethyl ester and 4-nitrobenzaldehyde gave Intermediate 45, the cis isomer as yellow crystals m.p.: 168° C. and Intermediate 46, the trans isomer as yellow crystals m.p.: 195° C.

Intermediate 47

Ethyl 1,2,3,4-tetrahydro-1-(4-dimethylaminophenyl)-9H-pyrido[3,4b]indole-3-carboxylate, mixture of cis and trans isomers The same method but starting from racemic tryptophan ethyl ester and 4-dimethylaminobenzaldehyde gave the title compound as white crystals m.p.: 170° C.

Intermediates 48 and 49

Ethyl 1,2,3,4-tetrahydro-1-(3-pyridyl)-9H-pyrido[3,4-b]indole-3-carboxylate, cis and trans isomers The same method but starting from racemic tryptophan ethyl ester and 3-pyridinecarboxaldehyde gave Intermediate 48, the cis isomer as pale yellow crystals m.p.: 230–232° C. and Intermediate 49, the trans isomer as white crystals m.p.: 210–214° C.

Intermediates 50 and 51

Methyl 1,2,3,4-tetrahydro-6-fluoro-1-(3,4-methylenedioxyphenyl)-9H-pyrido[3,4-b]indole-3-carboxylate, cis and trans isomers The same method but starting from racemic 5-fluoro-tryptophan methyl ester and piperonal gave Intermediate 50, the cis isomer as a cream solid m.p.: 60° C. and Intermediate 51, the trans isomer as a cream solid m.p.: 213° C.

Intermediates 52 and 53

Methyl 1,2,3,4-tetrahydro-6-fluoro-1-(4-methoxyphenyl)-9H-pyrido[3,4-b]indole-3-carboxylate, cis and trans isomers The same method but starting from racemic 5-fluoro-tryptophan methyl ester and 4-methoxybenzaldehyde gave Intermediate 52, the cis isomer as a solid $^1$H NMR (CDCl$_3$) δ (ppm): 7.4–6.8 (m, 8H, H aromatic); 5.15 (brs, 1H, H-1); 3.9 (dd, 1H, H-3) 3.8 (s, 3H, CO$_2$CH$_3$); 3.2–2.9 (m, 2H, H-4) and Intermediate 53, the trans isomer as a solid m.p.: 197° C.

Intermediates 54 and 55

(1R,3R)-Methyl 1,2,3,4-tetrahydro-1-(3,4-methylenedioxyphenyl)-9H-pyrido[3,4-b]indole-carboxylate, cis isomer and (1S,3R)-methyl 1,2,3,4-tetrahydro-1-(3,4-methylenedioxyphenyl)-9H-pyrido[3,4-b]indole-3-carboxylate trans isomer To a stirred solution of D-tryptophan methyl ester (11 g) and piperonal (7.9 g) in anhydrous CH$_2$Cl$_2$ (400 mL) cooled at 0° C. was added dropwise trifluoroacetic acid (7.7 mL) and the solution was allowed to react at ambient temperature. After 4 days, the yellow solution was diluted with CH$_2$Cl$_2$ (200 mL) and washed with a saturated aqueous solution of NaHCO$_3$, then with water (3×200 mL) and dried over Na$_2$SO$_4$. The organic layer was evaporated under reduced pressure and the residue was purified by flash chromatography eluting with dichloromethane/ethyl acetate (97/3) to give first Intermediate 54, the cis isomer (6.5 g) m.p.: 154° C. followed by Intermediate 55, the trans isomer (8.4 g) m.p.: 188° C.

The following compounds were obtained in a similar manner:

Intermediate 56

(1S,3S) Methyl-1,2,3,4-tetrahydro-1-(3,4-methylenedioxyphenyl)-9H-pyrido[3,4-b]indole-3-carboxylate, cis isomer and (1R,3S) methyl-1,2,3,4-tetrahydro-1-(3,4-methylenedioxyphenyl)-9H-pyrido[3,4-b]indole-3-carboxylate, trans isomer The same method but starting from L-tryptophan methyl ester and piperonal gave the cis and trans isomers of the title compound.

Cis isomer: white crystals m.p.: 154° C. Trans isomer: white crystals m.p.: 187–189° C.

Intermediates 57 and 58

(1R,3R)-Methyl 1,2,3,4-tetrahydro-1-(4-methoxyphenyl)-9H-pyrido[3,4-b]indole-3-carboxylate, cis isomer and (1S,3R)-methyl 1,2,3,4-tetrahydro-1-(4-methoxyphenyl)-9H-pyrido[3,4-b]indole-3-carboxylate, trans isomer The same method but starting from D-tryptophan methyl ester and 4-methoxybenzaldehyde gave Intermediate 57, the cis isomer as white crystals m.p.: 124–125° C. and Intermediate 58, trans isomer as white crystals m.p.: 219–222° C.

Intermediates 59 and 60

(1R,3R)-Methyl 1,2,3,4-tetrahydro-1-(3-chloro-4-methoxyphenyl)-9H-pyrido[3,4-b]indole-3-carboxylate, cis isomer and (1S,3R)-methyl 1,2,3,4-tetrahydro-1-(3-chloro-4-methoxyphenyl) 9H-pyrido[3,4-b]indole-3-carboxylate, trans isomer The same method, but starting from D-tryptophan methyl ester and 3-chloro-4-methoxybenzaldehyde gave Intermediate 59, the cis isomer isolated as the hydrochloride salt as white crystals m.p.: 200° C. and Intermediate 60, the trans isomer as white crystals m.p.: 164° C.

Intermediates 61 and 62

(1R,3R)-Methyl 1,2,3,4-tetrahydro-1-(2,3-dihydrobenzo[b]furan-5-yl)-9H-pyrido[3,4-b]indole-3-carboxylate, cis isomer and (1S,3R)-methyl 1,2,3,4-tetrahydro-1-(5-(2,3-dihydrobenzo[b]furan))-9H-pyrido[3,4-b]indole-3-carboxylate, trans isomer The same method but starting from D-tryptophan methyl ester and 2,3-dihydrobenzo[b]furan-5-carboxaldehyde gave Intermediate 61, the cis isomer as white crystals m.p.: 282° C. and Intermediate 62, the trans isomer as white crystals m.p.: 204° C.

Intermediates 63 and 64

(1R,3R)-Methyl 1,2,3,4-tetrahydro-1-(5-indanyl)-9H-pyrido[3,4-b]indole-3-carboxylate cis isomer and (1S,3R)-methyl 1,2,3,4-tetrahydro-1-(5-indanyl)-9H-pyrido[3,4-b]indole-3-carboxylate trans isomer The same method but starting from D-tryptophan methyl ester and indan-5-carboxaldehyde gave Intermediate 63, the cis isomer as white crystals m.p.: 130–131° C. and Intermediate 64, the trans isomer as white crystals m.p.: 196° C.

Intermediate 65

Ethyl 1,2,3,4-tetrahydro-1-(4-trifluoromethoxyphenyl)-9H-pyrido[3,4-b]indole-3-carboxylate, cis and trans isomers The same method but starting from racemic tryptophan ethyl ester and 4-trifluoromethylbenzaldehyde gave cis and trans isomers of the title compound.

Cis isomer: white crystals m.p.: 88° C. Trans isomer: white crystals m.p.: 152° C.

Intermediate 66

Methyl 1,2,3,4-tetrahydro-1-(5-methyl-2-thienyl)-9H-pyrido[3,4-b]indole-3-carboxylate, cis and trans isomers The same method but starting from racemic tryptophan methyl ester and 5-methyl-2-thiophenecarboxaldehyde gave the cis and trans isomers of the title compound.

Cis isomer: oily compound $^1$H NMR (CDCl$_3$) δ (ppm): 8.4 (brs, 1H, NH-indole); 7.7–6.6 (m, 6H, H aromatic); 5.5 (brs, 1H, H-1); 3.9 (dd, 1H, H-3); 3.85 (s, 3H, CO$_2$CH$_3$); 3.3–2.9 (m, 2H, H-4); 2.5 (s, 3H, CH$_3$). Trans isomer: white crystals m.p.: 194° C.

Intermediates 67 and 68

(1S,3R)-Methyl 1,2,3,4-tetrahydro-1-(3,4-methylenedioxyphenyl)-9H-pyrido[3,4-b]indole-3-carboxylate and (1R,3R)-methyl 1,2,3,4-tetrahydro-1-(3,4-methylenedioxyphenyl)-9H-pyrido[3,4-b]indole-3-carboxylate To a stirred solution of D-tryptophan methyl ester (obtained by treating the corresponding hydrochloride salt in water with saturated aqueous NaHCO$_3$ solution and extraction with CH$_2$Cl$_2$) (25.7 g) and piperonal (19.4 g) in anhydrous dichloromethane (700 ml) cooled to 0° C. was added dropwise trifluoroacetic acid (18.1 ml) and the solution was allowed to react at 4° C. After 5 days, the yellow solution was diluted with dichloromethane (500 ml). The organic layer was washed with a saturated aqueous solution of NaHCO$_3$, then with water (3×500 ml) until the pH was neutral and dried over Na$_2$SO$_4$. The organic layer was evaporated under reduced pressure to a volume of about 500 ml. The trans-isomer, which crystallised, was filtered and the filtrate was reduced to 200 ml. Another fraction of the trans-isomer crystallised. The fractions of trans-isomer were combined to give the (1S,3R) isomer, Intermediate 67, as white crystals (11.4 g).

mp: 188° C. $[\alpha]_D^{20°}$=+32.4° (c=1.03, CHCl$_3$).

The filtrate containing mainly the cis-isomer was reduced to 100 ml and isopropyl ether (200 ml) was added. Upon cooling, the (1R,3R) isomer, Intermediate 68, crystallised as a white solid (17.4 g).

mp: 154–55° C. $[\alpha]_D^{20°}$=+24.4° (c=1.03, CHCl$_3$).

Intermediate 69

(1R,3R)-Methyl 1,2,3,4-tetrahydro-1-(3,4-methylenedioxyphenyl)-9H-pyrido[3,4-b]indole-3-carboxylate Method A Intermediate 67 (5.0 g) was dissolved in methanol (150 ml). Hydrogen chloride was bubbled into the solution for several minutes at 0° C. and the resulting yellow solution was refluxed for 24 hours. The solvent was removed under reduced pressure and the residue was basified with a saturated aqueous solution of NaHCO$_3$ and extracted with dichloromethane. The organic layer was washed with water, dried over Na$_2$SO$_4$ and purified by flash chromatography eluting with dichloromethane/methanol (99/1) to give the title compound (2.3 g) corresponding to an authentic sample of Intermediate 68.

Method B

Intermediate 67 (25 g) was heated in 1N hydrochloric acid (78.5 ml) and water (400 ml) at 60°C. for 36 hours. From the initial pale yellow solution, a white solid precipitated. The mixture was then allowed to cool to 0° C. and the solid filtered. The solid was then washed with diisopropyl ether (3×200 ml) and dried to give the hydrochloride salt of the title compound (20 g) as a white solid.

mp (dec.): 209–212° C.

Method C

A 1:1 mixture of the cis and trans isomers of Intermediates 54 and 55 (2 g) was heated in 1N hydrochloric acid (6.8 ml) and water (15 ml) at 50° C. for 72 hours. A similar work-up as described in Method B above gave the hydrochloride salt of the title compound (1.7 g) as a white solid.

Intermediate 70

(R)-N$^\alpha$-(3,4-Methylenedioxyohenylcarbonyl)-tryptophan methyl ester

To a suspension of D-tryptophan methyl ester hydrochloride (10.2 g) in anhydrous CH$_2$Cl$_2$ (150 ml) cooled at 0° C. was added dropwise triethylamine (12.3 ml). To the resulting solution solid piperonyloyl chloride (8.16 g) was added portionwise at the same temperature, and the mixture was stirred at room temperature for 2 h. The mixture was washed successively with water, 0.5N hydrochloric acid, water, a saturated aqueous solution of NaHCO$_3$ and again with water. After drying over Na$_2$SO$_4$ and evaporation of the solvent under reduced pressure, the resulting oil on trituration from hot cyclohexane afforded the title compound as a white solid (14.7 g).

mp: 123–124° C. $[\alpha]_D^{20°}$=−84.4° (c=1.04, CHCl$_3$).

Intermediate 71

(R)-N$^\alpha$-(3,4-Methylenedioxyphenylthiocarbonyl)-tryptophan methyl ester

A mixture of Intermediate 70 (14 g) and Lawesson's reagent (9.289) in dimethoxyethane (280 ml) was heated at 60° C. under N$_2$ for 16 hours with stirring. The reaction mixture was evaporated to dryness and the resulting oil was dissolved in ethyl acetate, then washed successively with an aqueous saturated solution of NaHCO$_3$ and water and dried over Na$_2$SO$_4$. The oily residue obtained after evaporation under reduced pressure gave, on trituration from cyclohexane, a yellow powder which was filtered and washed with cooled methanol to afford the title compound (9.74 g).

mp: 129–130° C. $[\alpha]_D^{20°}$=−186.8° (c=1.14, CHCl$_3$).

Intermediate 72

(1R,3R)-Methyl 1,2,3,4-tetrahydro-1-(3,4-methylenedioxyphenyl)-9H-pyrido[3,4-b]indole-3-carboxylate A solution of Intermediate 71 (9 g) and methyl iodide (10 ml) in anhydrous dichloromethane (200 ml) was heated at reflux under an argon atmosphere with protection from light. After 24 hours, the solvent was removed under reduced pressure to give an orange oil which on trituration from hexane gave a solid which was washed with ether and used without further purification in the next step. This compound (13.11g) was dissolved in methanol (250 ml) and the solution was cooled to −78° C. NaBH$_4$ (0.99 g) was then added by portions and the mixture was stirred at the same temperature for 1 hour. The reaction was quenched by addition of acetone (10 ml) and the solvent was removed under reduced pressure. The residue was dissolved in CH$_2$Cl$_2$, washed with water and then with brine and dried over Na$_2$SO$_4$. After evaporation of the solvent, the orange oil gave on trituration from a hot mixture of diethyl ether/cyclohexane an orange powder which was recrystallised from diethyl ether/pentane to afford the title compound as a pale yellow solid (5.15 g) corresponding to an authentic sample of Intermediate 68.

Intermediate 73

(1R,3R)-Methyl 1,2,3,4-tetrahydro-2chloroacetyl-(3,4-methylenedioxyphenyl)-9H-pyrido[3,4-b]indole-3-carboxylate Method A To a stirred solution of Intermediate 72 (9.7 g) and NaHCO$_3$ (2.79 g) in anhydrous CHCl$_3$ (200 ml) was added dropwise chloroacetyl chloride (5.3 ml) at 0° C. under N$_2$. The resulting mixture was stirred for 1 hour at the same temperature and diluted with CHCl$_3$ (100 ml). Water (100 ml) was then added dropwise with stirring to the mixture, followed by a saturated aqueous solution of NaHCO$_3$. The organic layer was washed with water until neutrality and dried over Na$_2$SO$_4$. After evaporation of the solvent under reduced pressure, the oily compound obtained was crystallised from ether to give the title compound as a pale yellow solid (9.95 g).

mp: 233° C. $[\alpha]_D^{20°}$=−125.4° (c=1.17, CHCl$_3$).

Method B

Chloroacetyl chloride (4 ml) was added dropwide to a solution of Intermediate 72 (16.1 g) and triethylamine (7 ml) in anhydrous $CH_2Cl_2$ (200 ml) at 0° C. under $N_2$. The solution was stirred at 0° C. for 30 minutes, then diluted with $CH_2Cl_2$ (300 ml). The solution was washed with water (200 ml), a saturated aqueous solution of $NaHCO_3$ (300m1) and brine (400 ml). After drying over $Na_2SO_4$ and evaporation under reduced pressure, the resulting solid was washed with ether (300 ml) to give the title compound as a pale yellow solid (18.3 g).

Intermediate 74

Methyl 1,2,3,4-tetrahydro-6-methyl-1-(3,4-methylenedioxyphenyl)-9H-pyrido[3,4-b]indole-3-carboxylate, cis and trans isomers The cis and trans isomers of the title compound were prepared using the method described in Intermediate 1 but starting from racemic 5-methyl-tryptophan methyl ester and piperonal.

Cis isomer: yellow solid m.p.: 85° C. Trans isomer: yellow solid m.p.: 185° C.

Intermediates 75 and 76

(1R,3R)-Methyl 1,2,3,4-tetrahydro-1-(7-(4-methyl-3,4-dihydro-2H-benzo[1.4]oxazinyl))-9H-pyrido[3,4-b]indole-3-carboxylate, cis isomer and (1S,3R)-Methyl 1,2,3,4-tetrahydro-1-(7-(4-methyl-3,4-dihydro-2H-benzo[1.4]oxazinyl))-9H-pyrido[3,4-b]indole-3-carboxylate, trans isomer The same method, as described for intermediates 54 and 55, but starting from D-tryptophan methyl ester and 4-methyl-3,4-dihydro-2H-benzo[1,4]oxazine-7-carboxaldehyde gave Intermediate 75 the cis isomer as an oily compound $^1$H NMR ($CDCl_3$) δ (ppm): 7.6–7.1 (m, 5H); 6.9–6.6 (m, 3H); 5.15 (br s, 1H); 4.3 (t, 2H); 4 (dd, 1H); 3.8 (s, 3H); 3.3 (t, 2H); 3.3–2.95 (m, 2H); 2.9 (s, 3H); 1.6 (br s) and intermediate 76, the trans isomer as white crystals m.p.: 119–121° C.

Intermediate 77

Methyl 1,2,3,4-tetrahydro-1-(5-(N-benzylindolinyl))-9H-pyrido[3,4-b]indole-3-carboxylate, mixture of (1R,3R) and (1S,3R) isomers The same method, as described for intermediates 54 and 55, but starting from D-tryptophan methyl ester and N-benzylindoline-5-carboxaldehyde gave intermediate 77 as an oily compound.

Intermediates 78 and 79

(1R,3R)-Methyl 1,2,3,4-tetrahydro-1-(4carboheptoxyphenyl)-9H-pyrido[3,4-b]indole-3-carboxylate, cis isomer and (1S,3R)-methyl 1,2,3,4-tetrahydro-1-(4-carbomethoxyphenyl)-9H-pyrido[3,4-b]indole-3-carboxylate, trans isomer The same method, as described for intermediates 54 and 55, but starting from D-tryptophan methyl ester and methyl 4-formylbenzoate gave Intermediate 78, the cis isomer as white crystals m.p.: 157–160° C. and Intermediate 79, the trans isomer as pale yellow crystals m.p.: 124–126° C.

Intermediate 80

(1R,3R)-Methyl 1,2,3,4-tetrahydro-2-[2-(benzyloxycarbonyl)-R-prolyl]-1-(3,4-methylenedioxyphenyl)-9H-pyrido[3,4-b]indole-3-carboxylate A solution of N-(benzyloxycarbonyl)-D-proline acid chloride (0.64 g, 2.4 mmol) in anhydrous dichloromethane (10 mL) was added dropwise to a stirred solution of intermediate 54 (0.7 g, 2 mmol) and triethylamine (0.33 m; 2.4 mmol) in dichloromethane (15 mL) at −10° C. The mixture was stirred for 2 h at −10° C. after which it was diluted with dichloromethane (50 mL), washed with hydrochloric acid (1N), water, a saturated solution of $NaHCO_3$, a saturated NaCl solution and dried over $Na_2SO_4$. Evaporation of the solvent and recrystallisation of the crude product from methanol gave the title compound as pale yellow crystals (0.75 9) m.p.: 268–270° C.

Intermediate 81

(1R,3R)-Methyl 1,2,3,4-tetrahydro-2-[2-(benzyloxycarbonyl)-S-prolyl]-1-(3,4-methylenedioxyphenyl)-9H-pyrido[3,4-b]indole-3-carboxylate A solution of N-(benzyloxycarbonyl)-L-proline acid chloride (0.86 g, 3.2 mmol) in anhydrous dichloromethane (10 mL) was added dropwise to a stirred solution of intermediate 54 (0.91 g. 2.6 mmol) and triethylamine (0.44 mL, 3.2 mmol) in dichloromethane (20 mL) at −10° C. The mixture was stirred for 2 hours at −10° C. after which it was diluted with dichloromethane (60 mL), washed with hydrochloric acid (1 N), water, a saturated solution of $NaHCO_3$, a saturated NaCl solution and dried over $Na_2SO_4$. Evaporation of the solvent and recrystallisation of the crude product from menthol/water gave the title compound as pale yellow crystals (0.8 g) m.p.: 115–120° C.

Intermediate 82

(1R,3R)-Methyl 1,2,3,4-tetrahydro-2-(2-chloropropionyl)-1-(3,4-methylenedioxyphenyl)-9H-pyrido[3,4-b]indole-3-carboxylate To a solution of (S)-(−)-2-chloropropionic acid (87 μl, 1 mmol) in anhydrous dichloromethane (15 mL), was added dicyclohexylcarbodiimide (0.23 g, 1.1 mmol). Intermediate 54 (0.35 g, 1 mmol) was then added and the mixture was stirred at room temperature for 20 hours. The formed precipitate of dicyclohexylurea was removed by filtration, the filtrate was evaporated in vacuo and the crude product was purified by flash chromatography eluting with toluene/ethyl acetate: 95/5. The oily compound obtained was then crystallised from ether/hexane to give the title compound as pale yellow crystals (0.31 g) m.p.: 125–127° C.

Intermediate 83

(1R,3R)-Methyl 1,2,3,4-tetrahydro-2-(2-chloropropionyl)-1-3,4-methylenedioxyphenyl)-9H-pyrido[3,4-b]indole-3-carboxylate To a solution of (R)-(+)-2-chloropropionic acid (191 μl, 2.2 mmol) in anhydrous dichloromethane (30 mL), was added dicyclohexylcarbodiimide (0.45 g, 2.2. mol). Intermediate 54 (0.7 g, 2 mmol) was then added and the mixture was stirred at room temperature for 20 hours. The formed precipitate of dicyclohexylurea was removed by filtration, the filtrate was evaporated in vacuo and the crude product was purified by flash chromatography eluting with toluene/ethyl acetate: 95/5. The oily compound obtained was then crystallised from ether/hexane to give the title compound as pale yellow crystals (0.74 g) m.p.: 126–128° C.

Intermediates 84 and 85

(1R,3R)-Methyl 1,2,3,4-tetrahydro-1-(3,4dibenzyloxyphenyl)-9H-pyrido[3,4-b]indole-3-carboxylate cis isomer and (1S,3R)-methyl 1,2,3,4-tetrahydro-1-3,4-dibenzyloxyphenyl)-9H-pyrido[3,4-b]indole-3-carboxylate trans isomer The same method as described for intermediates 54 and 55 but starting from D-tryptophan methyl ester and 3,4- dibenzyloxybenzaldehyde gave intermediate 84, the cis isomer as an oily compound 1H NMR (CDCl$_3$) δ (ppm): 7.5–6.95 (m, 15H); 6.85 (s, 1H); 6.75 (s, 2H); 5.1 (s, 2H); 5 (br s, 1H); 4.95 (d, 2H) 3.85 (dd, 1H); 3.7 (s, 3H); 3.2–2.8 (m, 2H); 2.3 (br s, 1H) and intermediate 85, the trans isomer as an oily compound $^1$HNMR (CDCl$_3$) δ (ppm) 7.6–7 (m, 15H); 6.9–6.7 (m, 3H); 5.2 (br s, 1H); 5.1 (s, 2H); 5 (s, 2H); 3.8 (t, 1H); 3.65 (s, 3H); 3.3–3 (m, 2H); 2.25 (br s, 1H).

Intermediate 86

(6R,12aR)-2,3,6,7,12,12a-Hexahydro-6-(3,4-dibenzyloxyphenyl)-2-methyl-pyrazino[2',1': 6.1] pyrido[3,4-b]indole-1,4-dione The same two step procedure but starting from intermediate 84 and methylamine gave, after recrystallisation from dichloromethane/ether, the title compound as white crystals m.p.: 158–160° C., [α]$_D^{20°}$=+11.7° (c=1.23; CHCl$_3$).

Intermediate 87

Methyl 1,2,3,4-tetrahydro-1-(5-(2-methylisoindolinyl))-9H-pyrido[3,4-b]indole-3-carboxylate, mixture of (1R,3R) and (1S,3R) isomers The same method, as described for intermediates 54 and 55, but starting from D-tryptophan methyl ester and N-methylisoindoline-5-carboxaldehyde gave intermediate 87 as an oily compound.

EXAMPLE 1

Cis-2,3,6,7,12,12a-hexahydro-2-methyl-6-(3,4-methylenedioxyphenyl)-pyrazino[2',1':6,1]pyrido[3,4-b]indole-14-dione a) To a stirred solution of intermediate 1 (2 g) and NaHCO$_3$ (0.6 g) in anhydrous CHCl$_3$ (40 mL) was added dropwise chloroacetyl chloride (1.1 mL) at 0° C. The resulting mixture was stirred for 1 hour at the same temperature and diluted with CHCl$_3$. Water (20 mL) was then added dropwise with stirring to the mixture, followed by a saturated solution of NaHCO$_3$. The organic layer was washed with water until neutrality and dried over Na$_2$SO$_4$. After evaporation of the solvent under reduced pressure, cis-methyl 1,2,3,4-tetrahydro-2-chloroacetyl-1-(3,4-methylenedioxyphenyl)-9H-pyrido[3,4-b]indole-3-carboxylate was obtained as an oil which was crystallised from ether (2 g, m.p.: 215–218° C.) and was used without further purification in the next step.

b) To a stirred suspension of the chloroacetyl intermediate (0.34 g) in MeOH (20 mL) was added at ambient temperature a solution of methylamine (33% in EtOH) (0.37 mL) and the resulting mixture was heated at 50° C. under N$_2$ for 14 hours. The solvent was removed under reduced pressure and the residue was dissolved in CH$_2$Cl$_2$ (50 mL). After washing with water (3×30 mL), drying over Na$_2$SO$_4$ and evaporating to dryness, the residue was purified by flash chromatography eluting with CH$_2$Cl$_2$/MeOH (99/1) and recrystallised from MeOH to give the title compound as white crystals (0.19 g) m.p.: 253–255° C.

Analysis for C$_{22}$H$_{19}$N$_3$O$_4$: Calculated:C,67.86;H,4.92;N, 10.79; Found:C,67.53;H,4.99;N,10.62%.

The following compounds were obtained in a similar manner:

EXAMPLE 2

Cis-2,3,6,7,12,12a-hexahydro-2-butyl-10-fluoro-6-(4-methoxyphenyl)-pyrazino[2',1': 6.1]pyrido[3,4-b] indole-1,4-dione The same two step procedure but starting from butylamine and intermediate 52 gave, after recrystallisation from ethanol, the title compound as white crystals m.p.: 182° C.

Analysis for C$_{25}$H$_{26}$FN$_3$O$_3$ (0.1 H$_2$O): Calculated: C,68.67;H,6.04;N,9.61; Found: C,68.38;H,6.11;N,9.53%.

EXAMPLE 3

Trans-2,3,6,7,12,12a-hexahydro-2-methyl-6-(3,4-methylenedioxyphenyl)-pyrazino[2',1': 6.1]pyrido[3,4-b]indole-1,4-dione The same two step procedure but starting from methylamine and intermediate 2 gave, after recrystallisation from toluene, the title compound as white crystals m.p.: 301–303° C.

Analysis for C$_{22}$H$_{19}$N$_3$O$_4$: Calculated: C,67.86;H,4.92;N, 10.79; Found:C,67.98;H,4.98;N,10.73%.

EXAMPLE 4

Cis-2,3,6,7,12,12a-hexahydro-6-(3,4-methylenedioxyphenyl)-pyrazino[2',1': 6,1]pyrido[3,4-b]indole-1,4-dione The same two step procedure but starting from ammonia and intermediate 1 gave, after recrystallisation from methanol, the title compound as white crystals m.p.: 283–285° C.

Analysis for C$_{21}$H$_{17}$N$_3$O$_4$: Calculated: C,67.19;H,4.56;N, 11.19; Found:C,67.04;H,4.49;N,11.10%.

EXAMPLE 5

Cis-2,3,6,7,12,12a-hexahydro-10-fluoro-6-(4-methoxyphenyl)-2-(2,2,2-trifluoroethyl)-pyrazino[2', 1': 6.1]pyrido[3,4-b]indole-1,4-dione The same two step procedure but starting from 2,2,2-trifluoroethylamine and intermediate 52 gave, after recrystallisation from ethanol/diisopropyl ether, the title compound as white crystals m.p.: 190° C.

Analysis for C$_{23}$H$_{19}$F$_4$N$_3$O$_3$: Calculated: C,59.87;H, 4.15;N,9.11; Found: C,59.81;H,4.18;N,9.21%.

EXAMPLE 6

Cis-2,3,6,7,12,12a-hexahydro-10-fluoro-2-methyl6-(3,4methylenedioxyphenyl)-pyrazino[2',1': 6.1] pyrido[3,4-b]indole-1,4-dione The same two step procedure but starting from methylamine and intermediate 50 gave, after recrystallisation from ethanol, the title compound as white crystals m.p.: 292° C.

Analysis for C$_{22}$H$_{18}$FN$_3$O$_4$: Calculated: C,64.86;H, 4.45;N,10.31; Found: C,64.66;H,4.60;N,10.21%.

EXAMPLE 7

(6R,12aS)-2,3,6,7,12,12a-hexahydro-2-methyl-6-(3, 4-methylenedioxyphenyl)-pyrazino[2',1': 6.1]pyrido [3,4b]indole-1,4-dione The same two step procedure but starting from methylamine and the trans isomer of intermediate 56 gave, after recrystallisation from toluene, the title compound as white crystals m.p.: 287–289° C.

Analysis for C$_{22}$H$_{19}$N$_3$O$_4$ (0.25 toluene): Calculated: C,69.16;H,5.13;N,10.19; Found: C,69.09;H,5.14;N,10.19%. [α]$_D^{20°}$=−293.4° (C=1.28; CHCl$_3$).

EXAMPLE 8

(6S,12aR)-2,3,6,7,12,12a-hexahydro-2-methyl-6-(3, 4-methylenedioxyphenyl)-pyrazino[2',1': 6.1]pyrido [3,4b]indole-1,4-dione The same two step procedure but starting from methylamine and intermediate 55 gave, after recrystallisation from toluene, the title compound as white crystals m.p.: 287° C.

Analysis for $C_{22}H_{19}N_3O_4$ (0.3 toluene): Calculated: C,69.41;H,5.17;N,10.08; Found: C,69.56,H,5.24;N,10.08%. $[\alpha]_D^{20°}=+297.9°$ (C=1.21; CHCl$_3$).

EXAMPLE 9

Cis-2,3,6,7,12,12a-hexahydro-2-[2-(2-pyridyl)-ethyl]-6-3,4-methylenedioxyphenyl)pyrazino[2',1':6,1]pyrido[3,4-b]indole-1,4-dione The same two step procedure but starting from 2-2pyridyl)ethylamine and intermediate 1 gave, after recrystallisation from 2-propanol, the title compound as white crystals m.p.: 218–222° C.

Analysis for $C_{28}H_{24}N_4O_4$: Calculated: C,69.99;H,5.03;N, 11.66; Found: C,69.92;H,5.16;N,11.48%.

EXAMPLE 10

Cis-2,3,6,7,12,12a-hexahydro-2-(2-pyridylmethyl)-6-(3,4-methylenedioxyphenyl)-pyrazino[2',1':6,1]pyrido[3,4-b]indole-1,4-dione The same two step procedure but starting from 2-pyridylmethylamine and intermediate 1 gave, after recrystallisation from DMF/water, the title compound as cream crystals m.p: 285–286° C.

Analysis for $C_{27}H_{22}N_4O_4$ (0.4 H$_2$O): Calculated: C,68.46;H,4.85;N,11.83; Found: C,68.58;H,4.88;N,11.90%.

EXAMPLE 11

Cis-2,3,6,7,12,12a-hexahydro-2-3-pyridylmethyl)-6-(3,4-methylenedioxyphenyl)-pyrazino[2',1':6,1]pyrido[3,4-b]indole-1,4-dione The same two step procedure but starting from 3-pyridylmethylamine and intermediate 1 gave, after recrystallisation from CH$_2$Cl$_2$/MeOH, the title compound as cream crystals m.p.: 292–293° C.

Analysis: $C_{27}H_{22}N_4O_4$: Calculated: C,69.52;H,4.75;N, 12.01; Found: C,69.27;H,4.74;N,11.37%.

EXAMPLE 12

Cis-2,3,6,7,12,12a-hexahydro-2-(4-pyridylmethyl)-6-(3,4-methylenedioxyphenyl)-pyrazino[2',1':6,1]pyrido[3,4-b]indole-1,4-dione The same two step procedure but starting from 4-pyridylmethylamine and intermediate 1 gave, after recrystallisation from MeOH, the title compound as pale yellow crystals m.p.: 273–274° C.

Analysis for $C_{27}H_{22}N_4O_4$ (1.8 H$_2$O): Calculated: C,65.00;H,5.17;N,11.23; Found: C,65.11;H,4.85;N,11.07%.

EXAMPLE 13

Cis-2,3,6,7,12,12a-hexahydro-2-methyl-6-(3,4-methylenedioxyphenyl)-pyrazino[2',1':6,1]pyrido[3,4-b]indole-1,4-dione The same two step procedure but starting from ethylamine and intermediate 1 gave, after recrystallisation from methanol, the title compound as white crystals m.p.: 272–274° C.

Analysis for $C_{23}H_{21}N_3O_4$: Calculated: C,68.47;H,5.25;N, 10.42; Found:C,68.52;H,5.35;N,10.53%.

EXAMPLE 14

Cis-2,3,6,7,12,12a-hexahydro-2-(2,2,2-trifluoroethyl)-6-(3,4-methylenedioxyphenyl)-pyrazino[2',1':6,1]pyrido[3,4-b]indole-1,4-dione The same two step procedure but starting from 2,2,2-trifluoroethylamine and intermediate 1 gave, after recrystallisation from EtOH, the title compound as white crystals m.p.: 303° C.

Analysis for $C_{23}H_{18}F_3N_3O_4$: Calculated: C,60.40;H, 3.97;N,9.19; Found:C,60.43;H,4.15;N,9.16%.

EXAMPLE 15

Cis-2,3,6,7,12,12a-hexahydro-6-(3,4-methylenedioxyphenyl)-2-propyl-pyrazino[2',1':6,1]pyrido[3,4-b]indole-1,4-dione The same two step procedure but starting from propylamine and intermediate 1 gave, after recrystallisation from methanol, the title compound as white crystals m.p.: 270–271° C.

Analysis for $C_{24}H_{23}N_3O_4$: Calculated: C,69.05;H,5.55;N, 10.07; Found:C,69.22;H,5.50;N,9.80%.

EXAMPLE 16

Cis-2,3,6,7,12,12a-hexahydro-2-isopropyl-6-(3,4-methylenedioxyphenyl)-pyrazino[2',1':6,1]pyrido[3,4b]indole-1,4-dione The same two step procedure but starting from isopropylamine and intermediate 1 gave, after recrystallisation from methanol, the title compound as white crystals m.p.: 248–250° C.

Analysis for $C_{24}H_{23}N_3O_4$: Calculated: C,69.05;H,5.55;N, 10.07; Found:C,68.86;H,5.66;N,10.21%.

EXAMPLE 17

Cis-2,3,6,7,12,12a-hexahydro-2-cyclopropyl-6-(3,4-methylenedioxyphenyl)-pyrazino[2',1':6,1]pyrido[3,4b]indole-1,4-dione The same two step procedure but starting from cyclopropylamine and intermediate 1 gave, after recrystallisation from methanol, the title compound as white crystals m.p.: 290–292° C.

Analysis for $C_{24}H_{21}N_3O_4$: Calculated: C,69.39;H,5.10;N, 10.11; Found:C,69.1;H,5.20;N,9.94%.

EXAMPLE 18

Cis-2,3,6,7,12,12a-hexahydro-2-butyl-6-(3,4-methylenedioxyphenyl)-pyrazino[2',1':6,1]pyrido[3,4-b]indole-1,4-dione The same two step procedure but starting from butylamine and intermediate 1 gave, after recrystallisation from methanol/water, the title compound as white crystals m.p.: 241–243° C.

Analysis for $C_{25}H_{25}N_3O_4$: Calculated: C,69.59;H,5.84;N, 9.74; Found:C,69.77;H,5.82;N,9.81%.

EXAMPLE 19

Trans-2,3,6,7,12,12a-hexahydro-2-butyl-6-(3,4-methylenedioxyphenyl)-pyrazino[2',1':6,1]pyrido[3,4-b]indole-1,4-dione The same two step procedure but starting from butylamine and intermediate 2 gave, after recrystallisation from toluene, the title compound as white crystals m.p.: 243° C.

Analysis for $C_{25}H_{25}N_3O_4$: Calculated: C,69.59;H,5.84;N, 9.74; Found:C,69.80;H,5.78;N,9.52%.

EXAMPLE 20

Cis-2,3,6,7,12,12a-hexahydro-2-cyclopropylmethyl-6-(3,4-methylenedioxyphenyl)-pyrazino[2',1':6,1]pyrido[3,4-b]indole-1,4-dione The same two step procedure but starting from cyclopropylmethylamine and intermediate 1 gave, after recrystallisation from methanol, the title compound as white crystals m.p.: 217–218° C.

Analysis for $C_{25}H_{23}N_3O_4$: Calculated: C,69.92;H,5.40;N, 9.78; Found:C,70.02;H,5.47;N,9.84%.

EXAMPLE 21

Cis-2,3,6,7,12,12a-hexahydro-2-cyclopentyl-6-(3,4-methylenedioxyphenyl)-pyrazino[2',1':6,1]pyrido[3,4b]indole-1,4-dione The same two step procedure but starting from cyclopentylamine and intermediate 1 gave, after recrystallisation from acetone, the title compound as white crystals m.p.: 270° C.

Analysis for $C_{26}H_{25}N_3O_4$: Calculated: C,70.41;H,5.68;N, 9.47; Found:C,70.58;H,5.63;N,9.38%.

EXAMPLE 22

Cis-2,3,6,7,12,12a-hexahydro-2-cyclohexyl-6-(3,4-methylenedioxyphenyl)-pyrazino[2',1':6,1]pyrido[3,4-b]indole-1,4-dione The same two step procedure but starting from cyclohexylamine and intermediate 1 gave, after recrystallisation from menthol/water, the title compound as white crystals m.p.: 268–269° C.

Analysis for $C_{27}H_{27}N_3O_4$: Calculated: C,70.88;H,5.95;N, 9.18; Found:C,70.82;H,5.89;N,9.21%.

EXAMPLE 23

Cis-2,3,6,7,12,12a-hexahydro-2-benzyl-6-(3,4-methylenedioxyphenyl)-pyrazino[2',1':6,1]pyrido[3,4-b]indole-1,4-dione The same two step procedure but starting from benzylamine and intermediate 1 gave, after recrystallisation from dichloromethane/hexane, the title compound as white crystals m.p.: 285–287° C.

Analysis for $C_{28}H_{23}N_3O_4(1\ H_2O)$: Calculated: C,69.55;H,5.21;N,8.69; Found:C,69.30;H,5.06;N,8.48%.

EXAMPLE 24

Cis-2,3,6,7,12,12a-hexahydro-2-(4-fluorobenzyl)-6-(3,4-methylenedioxyphenyl)-pyrazino[2',1':6,1]pyrido[3,4b]indole-1,4-dione The same two step procedure but starting from 4-fluorobenzylamine and intermediate 1 gave, after recrystallisation from acetone, the title compound as white crystals m.p.: 281–283° C.

Analysis for $C_{28}H_{22}FN_3O_4$: Calculated: C,69.56;H, 4.59;F,3.93;N,8.69; Found:C69.54;H,4.58;F,3.82;N,8.63%.

EXAMPLE 25

Cis-2,3,6,7,12,12a-hexahydro-6-(4-methoxyphenyl)-2-methyl-pyrazino[2',1':6,1]pyrido[3,4-b]indole-1,4-dione The same two step procedure but starting from methylamine and intermediate 3 gave, after recrystallisation from 2-propanol, the title compound as white crystals m.p.: 257–263° C.

Analysis for $C_{22}H_{21}N_3O_3$: Calculated: C,70.38;H,5.64;N, 11.19; Found:C,70.11;H,5.55;N,11.15%.

EXAMPLE 26

Trans-2,3,6,7,12,12a-hexahydro-6-(4-methoxyphenyl)-2-methyl-pyrazino[2',1':6,1]pyrido[3,4-b]indole-1,4-dione The same two step procedure but starting from methylamine and intermediate 4 gave, after recrystallisation from diisopropyl ether, the title compound as white crystals m.p.: 225–228° C.

Analysis for $C_{22}H_{21}N_3O_3$: Calculated: C,70.38;H,5.64;N, 11.19; Found:C,70.34;H,5.77;N,11.19%.

EXAMPLE 27

Cis-2,3,6,7,12,12a-hexahydro-2-ethyl-6-(4-methoxyphenyl)-pyrazino[2',1':6,1]pyrido[3,4b]indole-1,4-dione The same two step procedure but starting from ethylamine and intermediate 3 gave, after recrystallisation from methanol, the title compound as white crystals m.p.: 245–255° C.

Analysis for $C_{23}H_{23}N_3O_3$: Calculated: C,70.93;H,5.95;N, 10.79; Found:C,70.74;H,6.06;N,10.87%.

EXAMPLE 28

Cis-2,3,6,7,12,12a-hexahydro-6-(4-methoxyphenyl)-2-(2,2,2-trifluoroethyl)pyrazino[2',1':6,1]pyrido[3,4-b]indole-1,4-dione The same two step procedure but starting from 2,2,2-trifluoroethylamine and intermediate 3 gave, after recrystallisation from ethanol, the title compound as white crystals m.p.: 232° C.

Analysis for $C_{23}H_{20}F_3N_3O_3$: Calculated: C,62.30;H, 4.55;N,9.48; Found:C,62.08;H,4.66;N,9.54%.

EXAMPLE 29

Cis-2,3,6,7,12,12a-hexahydro-2-butyl-6-(4-methoxyphenyl)-pyrazino[2',1':6,1]pyrido[3,4-b]indole-1,4-dione The same two step procedure but starting from butylamine and intermediate 3 gave, after recrystallisation from methanol,the title compound as white crystals m.p.: 157° C.

Analysis for $C_{25}H_{27}N_3O_3(0.5H_2O)$: Calculated: C,70.40;H,6.62;N,9.85; Found:C,70.25;H,6.60;N,9.83%.

EXAMPLE 30

Trans-2,3,6,7,12,12a-hexahydro-2-butyl-6-(4-methoxyphenyl)-pyrazino[2',1':6,1]pyrido[3,4b]indole-1,4-dione The same two step procedure but starting from butylamine and intermediate 4 gave, after recrystallisation from methanol, the title compound as white crystals m.p.: 212–214° C.

Analysis for $C_{25}H_{27}N_3O_3$: Calculated: C,71.92;H,6.52;N, 10.06; Found:C,71.81;H,6.55;N,10.03%.

EXAMPLE 31

Cis-2,3,6,7,12,12a-hexahydro-6-(4-methoxyphenyl)-2-cyclopropylmethyl-pyrazino[2',1':6,1]pyrido[3,4-b]indole-1,4-dione The same two step procedure but starting from cyclopropylmethylamine and intermediate 3 gave, after recrystallisation from methanol, the title compound as white crystals m.p.: 180–185° C.

Analysis for $C_{25}H_{25}N_3O_3$ (0.5$H_2O$): Calculated: C,70.74;H,6.17;N,9.90; Found:C,70.91;H,6.16;N,9.80%.

EXAMPLE 32

Cis-2,3,6,7,12,12a-hexahydro-2-benzyl-6-(4-methoxyphenyl)-pyrazino[2',1':6,1]pyrido[3,4-b]indole-1,4-dione The same two step procedure but starting from benzylamine and intermediate 3 gave, after recrystallisation from acetone, the title compound as white crystals m.p.: 275–279° C.

Analysis for $C_{28}H_{25}N_3O_3$: Calculated: C,74.48;H,5.58;N,9.31; Found:C,74.53;H,5.60;N,9.20%.

EXAMPLE 33

Cis-2,3,6,7,12,12a-hexahydro-6-(3-methoxyphenyl)-2-methyl-pyrazino[2',1':6,1]pyrido[3,4-b]indole-1,4-dione The same two step procedure but starting from methylamine and intermediate 5 gave, after recrystallisation from methanol, the title compound as white crystals m.p.: 267–269° C.

Analysis for $C_{22}H_{21}N_3O_3$: Calculated: C,70.38;H,5.64;N,11.19; Found:C,70.32;H,5.59;N,11.25%.

EXAMPLE 34

Cis-2,3,6,7,12,12a-hexahydro-6-(4-ethoxyphenyl)-2-methyl-pyrazino[2',1':6,1]pyrido[3,4b]indole-1,4-dione The same two step procedure but starting from methylamine and intermediate 6 gave, after recrystallisation from methanol, the title compound as white crystals m.p.: 247–248° C.

Analysis for $C_{23}H_{23}N_3O_3$: Calculated: C,70.93.H,5.95;N,10.79; Found:C,71.23;H,5.95;N,10.63%.

EXAMPLE 35

Cis-2,3,6,7,12,12a-hexahydro-6-(4-ethoxyphenyl)-2-cyclopropylmethyl-pyrazino[2',1':6,1]pyrido[3,4b]indole-1,4-dione The same two step procedure but starting from cyclopropylmethylamine and intermediate 6 gave, after recrystallisation from 2-propanol, the title compound as white crystals m.p.: 160–162° C.

Analysis for $C_{26}H_{27}N_3O_3$: Calculated: C,72.71;H,6.34;N,9.78; Found:C,72.28;H,6.39;N,9.71%.

EXAMPLE 36

Cis-2,3,6,7,12,12a-hexahydro-6-(2,3-dihydrobenzo[b]furan-5-yl)-2-methyl-pyrazino[2',1':6,1]pyrido[3,4-b]indole-1,4-dione The same two step procedure but starting from methylamine and intermediate 8 gave, after recrystallisation from methanol, the title compound as white crystals m.p.: 292–294° C.

Analysis for $C_{23}H_{21}N_3O_3$: Calculated: C,71.30;H,5.46;N,10.85; Found:C,71.15;H,5.56;N,10.84%.

EXAMPLE 37

Cis-2,3,6,7,12,12a-hexahydro-6-(2,3-dihydrobenzo[b]furan-5-yl-2-cyclopropylmethyl-pyrazino[2',1':6,1]pyrido[3,4-b]indole-1,4-dione The same two step procedure but starting from cyclopropylmethylamine and intermediate 8 gave, after recrystallisation from methanol, the title compound as white crystals m.p.: 165–166° C.

Analysis for $C_{26}H_{25}N_3O_3$: Calculated: C,73.05;H,5.89;N,9.83; Found:C,73.08;H,5.97;N,9.87%.

EXAMPLE 38

Cis-2,3,6,7,12,12a-hexahydro-6-(3,4-ethylenedioxyphenyl)-2-methyl-pyrazino[2',1':6,1]pyrido[3,4-b]indole-1,4-dione The same two step procedure but starting from methylamine and intermediate 10 gave, after recrystallisation from acetone, the title compound as white crystals m.p.: 303–305° C.

Analysis for $C_{23}H_{21}N_3O_4$: Calculated: C,68.47;H,5.25;N,10.42; Found:C,68.35;H,5.31;N,10.27%.

EXAMPLE 39

Cis-2,3,6,7,12,12a-hexahydro-6-(3,4-ethylenedioxyphenyl)-2-cyclopropylmethyl-pyrazino[2',1':6,1]pyrido[3,4-b]indole-1,4-dione The same two step procedure but starting from cyclopropylmethylamine and intermediate 10 gave, after recrystallisation from dichloromethane/ether, the title compound as white crystals m.p.: 288–290° C.

Analysis for $C_{26}H_{25}N_3O_4$: Calculated: C,70.41;H,5.68;N,9.47; Found:C,70.15;H,5.62;N,9.30%.

EXAMPLE 40

Cis-2,3,6,7,12,1 2a-hexahydro-2-butyl-6-(2-chlorophenyl)-pyrazino[2',1':6,1]pyrido[3,4-b]indole-1,4-dione The same two step procedure but starting from butylamine and intermediate 12 gave, after recrystallisation from methanol/water, the title compound as white crystals m.p.: 146° C.

Analysis for $C_{24}H_{24}ClN_3O_2$(0.75 $H_2O$): Calculated: C,66.20;H,5.90;N,9.65; Found:C,66.15;H,5.95;N,9.69%.

EXAMPLE 41

Cis-2,3,6,7,12,12a-hexahydro-6-chlorophenyl)-2-methyl-pyrazino[2',1':6,1]pyrido[3,4-b]indole-1,4-dione The same two step procedure but starting from methylamine and intermediate 13 gave, after recrystallisation from methanol, the title compound as white crystals m.p.: 274° C.

Analysis for $C_{21}H_{18}ClN_3O_2$ (0.25$H_2O$): Calculated: C,65.63;H,4.85;N,10.93; Found:C,65.39;H,4.84;N,10.85%.

EXAMPLE 42

Cis-2,3,6,7,12,12a-hexahydro-2-butyl-6-(4-chlorophenyl)-pyrazino[2',1':6,1]pyrido[3,4-b]indole-1,4-dione The same two step procedure but starting from butylamine and intermediate 13 gave, after recrystallisation from ethanol/water, the title compound as white crystals m.p.: 164–166° C.

Analysis for $C_{24}H_{24}ClN_3O_2$: Calculated: C,68.32;H, 5.73;Cl,8.40;N,9.96; Found:C,68.48;H,5.64;Cl,8.37;N, 9.99%.

EXAMPLE 43

Cis-2,3,6,7,12,12a-hexahydro-6-(4-dichlorophenyl)-2-methyl-pyrazino[2',1':6,1]pyrido[3,4-b]indole-1,4-dione The same two step procedure but starting from methylamine and intermediate 15 gave, after recrystallisation from ethanol/DMF, the title compound as white crystals m.p.: >260° C.

Analysis for $C_{21}H_{17}Cl_2N_3O_2$ (0.5 $H_2O$): Calculated: C,59.39;H,4.29;N,9.93; Found:C,59.32;H,4.16;N,9.99%.

EXAMPLE 44

Cis-2,3,6,7,12,12a-hexahydro-2-butylphenyl-pyrazino[2',1':6,1]pyrido[3,4-b]indole-1,4-dione The same two step procedure but starting from butylamine and cis-methyl 1,2,3,4-tetrahydro-1-phenyl-9H-pyrido[3,4-b]indole-3-carboxylate[1] gave, after recrystallisation from methanol/water, the title compound as white crystals m.p.: 243–245° C.

Analysis for $C_{24}H_{25}N_3O_2$: Calculated: C,74.39;H,6.50;N, 10.84; Found:C,74.54;H,6.51;N,10.86%. 1. D. Soerens et al., J. Org. Chem. 44, 535–545 (1979).

EXAMPLE 45

Cis-2,3,6,7,12,12a-hexahydro-2-benzyl-6-phenyl-pyrazino[2',1':6,1]pyrido[3,4-b]indole-1,4-dione The same two step procedure but starting from benzylamine and cis-methyl-1,2,3,4-tetrahydro-1-phenyl-9H-pyrido[3,4-b]indole-3-carboxylate gave, after recrystallisation from methanol, the title compound as white crystals m.p.: 193–195° C.

Analysis for $C_{27}H_{23}N_3O_2$: Calculated: C,76.94;H,5.50;N, 9.97; Found:C,77.23;H,5.54;N,9.97%.

EXAMPLE 46

Trans-2,3,6,7,12,12a-hexahydro-2-benzyl-6-phenyl-pyrazino[2',1':6,1]pyrido[3,4-b]indole-1,4-dione The same two step procedure but starting from benzylamine and cis-methyl-1,2,3,4-tetrahydro-1-phenyl-9H-pyrido[3,4-b]indole-3-carboxylate gave, after recrystallisation from methanol, the title compound as white crystals m.p.: 284° C.

Analysis for $C_{27}H_{23}N_3O_2$: Calculated: C,76.94;H,5.50;N, 9.97; Found:C,76.88;H,5.45;N,9.89%.

EXAMPLE 47

Cis-2,3,6,7,12,12a-hexahydro-2-methyl-6-(1,2,3,4-tetrahydro-6-naphthyl)-pyrazino[2',1':6,1]pyrido[3,4-b]indole-1,4-dione The same two step procedure but starting from methylamine and intermediate 17 gave, after recrystallisation from methanol, the title compound as white crystals m.p.: >260° C.

Analysis for $C_{25}H_{25}N_3O_2$: Calculated: C,75.16;H,6.31;N, 10.52; Found:C,74.93;H,6.43;N,10.63%.

EXAMPLE 48

Cis-2,3,6,7,12,12a-hexahydro-2-isopropyl-6-(1,2,3,4-tetrahydro-6-naphthyl)-pyrazino[2',1':6,1]pyrido[3,4-b]indole-1,4-dione The same two step procedure but starting from isopropylamine and intermediate 17 gave, after recrystallisation from the title compound as off-white crystals m.p.: 244–246° C.

Analysis for $C_{27}H_{29}N_3O_2$ (0.25$H_2O$): Calculated: C,75.06;H,6.88;N,9.73; Found:C,75.00;H,6.83;N,9.69%.

EXAMPLE 49

Cis-2,3,6,7,12,12a-hexahydro-2-cyclopropylmethyl-6-(1,2,3,4-tetrahydro-6-naphthyl))-pyrazino[2',1':6,1]pyrido[3,4-b]indole-1,4-dione The same two step procedure but starting from cyclopropylmethylamine and intermediate 17 gave, after recrystallisation from ethanol/pentane, the title compound as white crystals m.p.: 125° C.

Analysis for $C_{28}H_{29}N_3O_2$ (0.25$H_2O$): Calculated: C,75.73;H,6.70;N,9.46; Found:C,75.45;H,6.86;N,9.14%.

EXAMPLE 50

Cis-2,3,6,7,12,12a-hexahydro-2-methyl-6-(2-naphthyl)-pyrazino[2',1':6,1]pyrido[3,4-b]indole-1,4-dione The same two step procedure but starting from methylamine and intermediate 18 gave, after recrystallisation from dichloromethane/methanol, the title compound as white crystals m.p.: >260° C.

Analysis for $C_{25}H_{21}N_3O_2$ (0.25$H_2O$): Calculated: C,75.08;H,5.42;N,10.51; Found:C,75.35;H,5.42;N,10.49%.

EXAMPLE 51

Cis-2,3,6,7,12,12a-hexahydro-2-butyl-6-(2-thienyl)-pyrazino[2',1':6,1]pyrido[3,4-b]indole-1,4-dione The same two step procedure but starting from butylamine and intermediate 20 gave, after recrystallisation from ethanol, the title compound as white crystals m.p.: 226° C.

Analysis for $C_{22}H_{23}N_3O_2S$: Calculated: C,67.15;H, 5.89;N,10.68; Found:C,67.39;H,5.88;N,10.77%.

EXAMPLE 52

Cis-2,3,6,7,12,12a-hexahydro-6-(5-bromo-2-thienyl)-2-methyl-pyrazino[2',1':6,1]pyrido[3,4-b]indole-1,4-dione The same two step procedure but starting from methylamine and intermediate 24 gave, after recrystallisation from ethanol, the title compound as a cream powder m.p.: 258° C.

Analysis for $C_{19}H_{16}BrN_3O_2S$: Calculated: C,53.03;H, 3.75;N,9.76; Found:C,53.01;H,3.78;N,9.69%.

EXAMPLE 53

Cis-2,3,6,7,12,12a-hexahydro-6-(4-bromo-2-thienyl)-2-methyl-pyrazino[2',1':6,1]pyrido[3,4-b]indole-1,4-dione The same two step procedure but starting from methylamine and intermediate 26 gave, after recrystallisation from ethanol, the title compound as white crystals mp.: 292° C.

Analysis for $C_{19}H_{16}BrN_3O_2S$ (0.25$H_2O$): Calculated: C,52.48;H,3.82;N,9.66; Found:C,52.46;H,3.81;N,9.60%.

EXAMPLE 54

Cis-2,3,6,7,12,12a-hexahydro-6-(5-bromo-2-thienyl)-2-cyclopropylmethyl-pyrazino[2',1':6,1]pyrido[3,4-b]indole-1,4-dione The same two step procedure but starting from cyclopropylmethylamine and intermediate 24 gave, after recrystallisation from ethanol, the title compound as white crystals m.p.: 190° C.

Analysis for $C_{22}H_{20}BrN_3O_2S$: Calculated: C,56.18;H, 4.29;N,8.93; Found:C,55.92;H,4.28;N,8.74%.

EXAMPLE 55

Cis-2,3,6,7,12,12a-hexahydro-6-(5-bromo-2-thienyl)-2-cyclopentyl-pyrazino[2',1':6,1]pyrido[3,4-b]indole-1,4-dione The same two step procedure but starting from cyclopentylamine and intermediate 24 gave, after recrystallisation from ethanol, the title compound as white crystals m.p.: 252° C.

Analysis for $C_{23}H_{22}BrN_3O_2S$: Calculated: C,57.03;H, 4.58;N,8.67; Found:C,56.87;H,4.66;N,8.68%.

EXAMPLE 56

Cis-2,3,6,7,12,12a-hexahydro-2-methyl-6-(5-methyl-2-thienyl)-pyrazino[2',1':6,1]pyrido[3,4b]indole-1,4-dione The same two step procedure but starting from methylamine and the cis isomer of intermediate 66 gave, after recrystallisation from ethanol, the title compound as white crystals m.p.: 282° C.

Analysis for $C_{20}H_{19}N_3O_2S$ (0.25$H_2O$): Calculated: C,64.93;H,5.31;N,11.36; Found:C,64.84;H,5.28;N,10.81%.

EXAMPLE 57

Cis-2,3,6,7,12,12a-hexahydro-2-methyl-6-(3-thienyl)-pyrazino[2',1':6,1]pyrido[3,4b]indole-1,4-dione The same two step procedure but starting from methylamine and intermediate 22 gave, after recrystallisation from acetone, the title compound as white crystals m.p.: 290–295° C.

Analysis for $C_{19}H_{17}N_3O_2S$: Calculated: C,64.94;H, 4.88;N,11.96; Found: C,64.81;H,4.95;N,11.68%.

EXAMPLE 58

Cis-2,3,6,7,12,12a-hexahydro-2-butyl-6-(3-thienyl)-pyrazino[2',1':6,1]pyrido[3,4-b]indole-1,4-dione The same two step procedure but starting from butylamine and intermediate 22 gave, after recrystallisation from methanol, the title compound as white crystals m.p.: 236–239° C.

Analysis for $C_{22}H_{23}N_3O_2S$: Calculated: C,67.15;H, 5.89;N,10.68;S,8.15; Found:C,67.42;H,5.76;N,10.57;S, 8.01%.

EXAMPLE 59

Cis-2,3,6,7,12,12a-hexahydro-2-methyl-6-(3-furyl)-pyrazino[2',1':6,1]pyrido[3,4-b]indole-1,4-dione The same two step procedure but starting from methylamine and the cis isomer of intermediate 28 gave, after recrystallisation from ether, the title compound as a white solid m.p.: 250° C.

Analysis for $C_{19}H_{17}N_3O_3$ (0.5$H_2O$): Calculated: C,66.27;H,5.27;N,12.20; Found:C,66.33;H,5.48;N,12.02%.

EXAMPLE 60

Cis-2,3,6,7,12,12a-hexahydro-2-methyl-6-(5-methyl-2-furyl)-pyrazino[2',1':6,1]pyrido[3,4-b]indole-1,4-dione The same two step procedure but starting from methylamine and intermediate 29 gave, after recrystallisation from ethanol, the title compound as a cream powder m.p.: 303° C.

Analysis for $C_{20}H_{19}N_3O_3$ (0.25$H_2O$): Calculated: C,67.88;H,5.55;N,11.87; Found:C,67.90;H.5.50;N,11.98%.

EXAMPLE 61

Cis-2,3,6,7,12,12a-hexahydro-2-methyl-6-(4-methylphenyl)-pyrazino[2',1':6,1]pyrido[3,4-b]indole-1,4-dione The same two stop procedure but starting from methylamine and intermediate 31 gave, after recrystallisation from ethanol, the title compound as white crystals m.p.: >260° C.

Analysis for $C_{22}H_{21}N_3O_2$ (0.25$H_2O$): Calculated: C,72.61;H,5.95;N,11.55; Found:C,72.73;H,5.96;N,1.59%.

EXAMPLE 62

Cis-2,3,6,7,12,12a-hexahydro-2-isopropyl-6-(4-methylphenyl)-pyrazino[2',1':6,1]pyrido[3,4-b]indole-1,4-dione The same two step procedure but starting from isopropylamine and intermediate 31 gave, after recrystallisation from the title compound as white crystals m.p.: 170° C.

Analysis for $C_{24}H_{25}N_3O_2$ (0.5$H_2O$): Calculated: C,72.70;H,6.61;N,10.60; Found:C,73.06;H,6.43;N,9.66%.

EXAMPLE 63

Cis-2,3,6,7,12,12a-hexahydro-2-butyl-6-(4-methylphenyl)-pyrazino[2',1':6,1]pyrido[3,4-b]indole-1,4-dione The same two step procedure but starting from butylamine and intermediate 31 gave, after recrystallisation from methanol, the title compound as white crystals m.p.: 194° C.

Analysis for $C_{25}H_{27}N_3O_2$ (0.5$H_2O$): Calculated: C,73.15;H,6.87;N,10.24; Found:C,73.01;H,6.84.N,10.26%.

EXAMPLE 64

Cis-2,3,6,7,12,1 2a-hexahydro-2-cyclopropylmethyl-6-(4-methylphenyl)-pyrazino[2',1':6,1]pyrido[3,4b]indole-1,4-dione The same two step procedure but starting from cyclopropylmethylamine and intermediate 31 gave, after recrystallisation from methanol/water, the title compound as white crystals m.p.: 194° C.

Analysis for $C_{25}H_{25}N_3O_2$ (1.1$H_2O$): Calculated: C,71.61;H,6.54;N,10.02; Found:C,71.42;H,6.07;N,9.95%.

EXAMPLE 65

Cis-2,3,6,7,12,12a-hexahydro-2-methyl-6-(3-methylphenyl)-pyrazino[2',1':6,1]pyrido[3,4-b]indole-1,4-dione The same two step procedure but starting from methylamine and intermediate 33 gave, after recrystallisation from ethanol, the title compound as white crystals m.p.: >260° C.

Analysis for $C_{22}H_{21}N_3O_2$: Calculated: C,73.52;H,5.89;N, 11.69; Found:C,73.60;H,5.97;N,11.66%.

EXAMPLE 66

Cis-2,3,6,7,12,12a-hexahydro-2-butyl-6-(4-trifluoromethylphenyl)-pyrazino[2',1':6,1]pyrido[3,4-b]indole-1,4-dione The same two step procedure but starting from butylamine and intermediate 35 gave, after recrystallisation from methanol/water, the title compound as white crystals m.p.: 155° C.

Analysis for $C_{25}H_{24}F_3N_3O_2$ (0.5H$_2$O): Calculated: C,64.65;H,5.43;N,9.05; Found:C,64.78;H,5.40;N,9.01%.

EXAMPLE 67

Cis-2,3,6,7,12,12a-hexahydro-2-methyl-6-(4-trifluoromethoxyphenyl)-pyrazino[2',1':6,1]pyrido[3,4-b]indole-1,4-dione The same two step procedure but starting from methylamine and the cis isomer of intermediate 65 gave, after recrystallisation from methanol, the title compound as white crystals m.p.: 174–180° C.

Analysis for $C_{22}H_{18}F_3N_3O_3$ (0.5H$_2$O): Calculated: C,60.27;H,4.37;N,9.58; Found:C,60.24;H,4.28;N,9.50%.

EXAMPLE 68

Cis-2,3,6,7,12,12a-hexahydro-2-methyl-6-(4-hydroxyphenyl)-pyrazino[2',1':6,1]pyrido[3,4-b]indole-1,4-dione The same two step procedure but starting from methylamine and intermediate 39 gave, after recrystallisation from methanol, the title compound as yellow crystals m.p.: 179–180° C.

Analysis for $C_{21}H_{19}N_3O_3$(1.25H$_2$O): Calculated: C,65.70;H,5.64;N,10.94; Found:C,65.46;H,5.45;N,10.92%.

EXAMPLE 69

Cis-2,3,6,7,12,12a-hexahydro-6-(3-hydroxy-4-methoxyphenyl)-2-methyl-pyrazino[2',1':6,1]pyrido[3,4-b]indole-1,4-dione The same two step procedure but starting from methylamine and intermediate 40 gave, after recrystallisation from ethanol, the title compound as white crystals m.p.: 320° C.

Analysis for $C_{22}H_{21}N_3O_4$ (0.25H$_2$O): Calculated: C,66.74;H,5.47;N,10.61; Found:C,66.72;H,5.46;N,10.53%.

EXAMPLE 70

Cis-2,3,6,7,12,12a-hexahydro-6-(4-hydroxy-3-methoxyphenyl)-2-methyl-pyrazino[2',1':6,1]pyrido[3,4-b]indole-1,4-dione The same two step procedure but starting from methylamine and intermediate 41 gave, after recrystallisation from dichloromethane/ethanol, the title compound as yellow crystals m.p.: 264–265° C.

Analysis for $C_{22}H_{21}N_3O_4$: Calculated: C,67.51;H,5.41;N, 10.74; Found:C,67.05;H,5.41;N,10.62%.

EXAMPLE 71

Cis-2,3,6,7,12,12a-hexahydro-2-butyl-6-(4-cyanophenyl)-pyrazino[2',1':6,1]pyrido[3,4b]indole-1,4-dione The same two step procedure but starting from butylamine and intermediate 37 gave, after recrystallisation from methanol/water, the title compound as white crystals m.p.: 246° C.

Analysis for $C_{25}H_{24}N_4O_2$ (1H$_2$O): Calculated: C,69.75;H,6.09;N,13.01; Found:C,69.50;H,5.96;N,12.86%.

EXAMPLE 72

Cis-2,3,6,7,12,12a-hexahydro-6-(4-ethylphenyl)-2-isopropyl-pyrazino[2',1':6,1]pyrido[3,4b]indole-1,4-dione The same two step procedure but starting from isopropylamine and the cis isomer of intermediate 42 gave, after recrystallisation from n-pentane, the title compound as white crystals m.p.: 130° C.

Analysis for $C_{25}H_{27}N_3O_2$ (0.5H$_2$O): Calculated: C,73.15;H,6.87;N,10.24; Found:C,73.39;H,7.08;N,9.81%.

EXAMPLE 73

Cis-2,3,6,7,12,12a-hexahydro-6-(4-ethylphenyl)-2-cyclopropylmethyl-pyrazino[2',1':6,1]pyrido[3,4-b]indole-1,4-dione The same two step procedure but starting from cyclopropylmethylamine and the cis isomer of intermediate 42 gave, after recrystallisation from ethanol, the title compound as white crystals m.p.: 160° C.

Analysis for $C_{26}H_{27}N_3O_2$: Calculated: C,75.52;H,6.58;N, 10.16; Found:C,75.54;H,6.62;N,10.08%.

EXAMPLE 74

Cis-2,3,6,7,12,12a-hexahydro-6-(4-isopropylphenyl)-2-methyl-pyrazino[2',1':6,1]pyrido[3,4-b]indole-1,4-dione The same two step procedure but starting from methylamine and intermediate 43 gave, after recrystallisation from ethanol, the title compound as white crystals m.p.: 244° C.

Analysis for $C_{24}H_{25}N_3O_2$: Calculated: C,74.39;H,6.50;N, 10.84; Found:C,74.27;H,6.53;N,11.05%.

EXAMPLE 75

Cis-2,3,6,7,12,12a-hexahydro-2-butyl-6-(4-nitrophenyl)-pyrazino[2',1':6.1]pyrido[3,4-b]indole-1,4-dione The same two step procedure but starting from butylamine and intermediate 45 gave, after recrystallisation from methanol, the title compound as white crystals m.p.: 182° C.

Analysis for $C_{24}H_{24}N_4O_4$ (0.25H$_2$O): Calculated: C,65.97;H,5.65;N,12.82; Found:C,65.92;H,5.62;N,12.96%.

EXAMPLE 76

Cis-2,3,6,7,12,12a-hexahydro-6-(4-dimethylaminophenyl)-2-methyl-pyrazino[2',1':6,1]pyrido[3,4b]indole-1,4-dione The same two step procedure but starting from methylamine and the cis isomer of intermediate 47 gave after recrystallisation from methanol, the title compound as white crystals m.p.: 266° C.

Analysis for $C_{23}H_{24}N_4O_2$: Calculated: C,71.11;H,6.23;N, 14.42; Found:C,71.19;H,6.24;N,14.34%.

EXAMPLE 77

Cis-2,3,6,7,12,12a-hexahydro-2-methyl-6-(3-pyridyl)-pyrazino[2',1':6,1]pyrido[3,4b]indole-1,4-dione The same two step procedure but starting from methylamine and intermediate 48 gave after recrystallisation from chloroform, the title compound as white crystals m.p.: 312° C.

EXAMPLE 78

(6R,12aR)-2,3,6,7,12,12a-Hexahydro-2-methyl-6-(3,4-methylenedioxyphenyl)-pyrazino[2',1':6,1]pyrido[3,4-b]indole-1,4-dione a) To a stirred solution of intermediate 54 (0.5 g) and NaHCO$_3$ (0.14 g) in anhydrous CHCl$_3$ (20 mL) was added dropwise chloroacetyl chloride (0.27 mL) at 0° C. The resulting mixture was stirred for 1 hour at the same temperature and diluted with CHCl$_3$ (20 mL). Water (10 mL) was then added dropwise with stirring to the mixture, followed by a saturated solution of NaHCO$_3$. The organic layer was washed with water until neutrality and dried over Na$_2$SO$_4$. After evaporation of the solvent under reduced pressure, (6R,12aR)-methyl 1,2,3,4-tetrahydro-2-chloroacetyl-1-( 3,4-methylenedioxyphenyl)-9H-pyrido[3,4-b]indole-3-carboxylate was obtained as an oil which was crystallised from ether to give a solid (0.38 g, m.p.: 233° C.) which was used without further purification in the next step.

b) To a stirred suspension of the chloroacetyl intermediate (0.37 g) in MeOH (20 mL) was added at room temperature a solution of methylamine (33% in EtOH) (0.4 mL) and the resulting mixture was heated at 50° C. under N$_2$ for 16 hours. The solvent was removed under reduced pressure and the residue was dissolved in CH$_2$Cl$_2$ (50 mL). After washing with water (3×20 mL), drying over Na$_2$SO$_4$ and evaporating to dryness, the residue was purified by flash chromatography eluting with CH$_2$Cl$_2$/MeOH (9911) and recrystallised from 2-propanol to give the title compound as white crystals (0.22 g) m.p.: 302–303° C.

Analysis for C$_{22}$H$_{19}$N$_3$O$_4$: Calculated:C,67.86;H,4.92;N, 10.79; Found:C,67.77;H,4.92;N,10.74%. [α]$_D^{20°}$=+71.0° (C=1.00; CHCl$_3$).

The following compounds were obtained in a similar manner:

EXAMPLE 79

(6R,12aR)-2,3,6,7,12,12a-Hexahydro-2-isopropyl-6-(3,4-methylenedioxyphenyl)-pyrazino[2',1':6,1]pyrido[3,4-b]indole-1,4-dione The same two step procedure but starting from isopropylamine and intermediate 54 gave, after recrystallisation from methanol, the title compound as white crystals m.p.: 290–293° C.

Analysis for C$_{24}$H$_{23}$N$_3$O$_4$: Calculated: C,69.05;H,5.55;N, 10.07; Found:C,69.06;H,5.49;N,10.12%. [α]$_D^{20°}$=+52.6° (C=1.14; CHCl$_3$).

EXAMPLE 80

(6R,12aR)-2,3,6,7,12,12a-Hexahydro-2-butyl-6-(3,4-methylenedioxyphenyl)-pyrazino[2',1':6,1]pyrido[3,4b]indole-1,4-dione The same two step procedure but starting from butylamine and intermediate 54 gave, after recrystallisation from toluene/hexane, the title compound as white crystals m.p.: 209–210° C.

Analysis for C$_{25}$H$_{25}$N$_3$O$_4$: Calculated: C,69.59;H,5.84;N, 9.74; Found:C,69.70;H,5.93;N,9.74%. [α]$_D^{20°}$=+50.2° (C=0.53; CHCl$_3$).

EXAMPLE 81

(6R,12aR)-2,3,6,7,12,12a-Hexahydro-2-isobutyl-6-(3,4-methylenedioxyphenyl)-pyrazino[2',1':6,1]pyrido[3,4-b]indole-1,4-dione The same two step procedure but starting from isobutylamine and intermediate 54 gave, after recrystallisation from methanol, the title compound as white crystals m.p.: 227–228° C.

Analysis for C$_{25}$H$_{25}$N$_3$O$_4$: Calculated: C,69.59;H,5.84;N, 9.74; Found:C,69.52;H,5.87;N,9.74%. [α]$_D^{20°}$=+45° (C=1.04; CHCl$_3$).

EXAMPLE 82

(6R,12aR)-2,3,6,7,12,12a-Hexahydro-2-cyclopentyl-6-(3,4-methylenedioxyphenyl)-pyrazino[2',1':6,1]pyrido[3,4-b]indole-1,4-dione The same two step procedure but starting from cyclopentylamine and intermediate 54 gave, after recrystallisation from ether, the title compound as white crystals m.p.: 237–239° C.

Analysis for C$_{26}$H$_{25}$N$_3$O$_4$: Calculated: C,70.41;H,5.68;N, 9.47; Found:C,70.13.H,5.67.N,9.42%. [α]$_D^{20°}$=+36.6° (C=0.98; CHCl$_3$).

EXAMPLE 83

(6R,12aR)-2,3,6,7,12,12a-Hexahydro-6-(3,4-methylenedioxyphenyl)-2-cyclohexylmethyl-pyrazino[2',1':6,1]pyrido[3,4-b]indole-1,4-dione The same two step procedure but starting from cyclohexylmethylamine and the cis isomer of intermediate 56 gave, after recrystallisation from 2propanol the title compound as white crystals m.p.: 209° C.

Analysis for C$_{28}$H$_{29}$N$_3$O$_4$: Calculated: C,71.32;H,6.20;N, 8.91; Found:C,71.30;H,6.29;N,8.74%. [α]$_D^{20°}$=+40.0° (C=0.99; CHCl$_3$).

EXAMPLE 84

(6R,12aR)-2,3,6,7,12,12a-Hexahydro-2-cyclopropylmethyl-6-(4-methoxyphenyl)-pyrazino[2',1':6,1]pyrido[3,4b]indole-1,4-dione The same two step procedure but starting from cyclopropylmethylamine and intermediate 57 gave, after recrystallisation from methanol, the title compound as white crystals m.p.: 204–205° C.

Analysis for C$_{25}$H$_{25}$N$_3$O$_3$ (0.5H$_2$O): Calculated: C,70.74;H,6.17;N,9.90; Found:C,70.98;H,6.09;N,9.92%. [α]$_D^{20°}$=+54.1° (C=1.03; CHCl$_3$).

EXAMPLE 85

(6R,12aR)-2,3,6,7,12,12a-Hexahydro-2-butyl-6-(4-methoxyphenyl)-pyrazino[2',1':6,1]pyrido[3,4b]indole-1,4-dione The same two step procedure but starting from butylamine and intermediate 57 gave, after recrystallisation from 2-propanol, the title compound as white crystals m.p.: 183–184° C.

Analysis for C$_{25}$H$_{27}$N$_3$O$_3$ (0.5H$_2$O): Calculated: C,70.40;H,6.62;N,9.85; Found:C,70.55;H,6.64;N,9.92%. [α]$_D^{20°}$=+45.4° (C=1.04; CHCl$_3$).

EXAMPLE 86

(6R,12aR)-2,3,6,7,12,12a-Hexahydro-2-cyclopentyl-6-(4-methoxyphenyl)-pyrazino[2',1':6,1]pyrido[3,4-b]indole-1,4-dione The same two step procedure but starting from cyclopentylamine and intermediate 57 gave, after recrystallisation from ether, the title compound as white crystals m.p.: 210–211° C.

Analysis for C$_{20}$H$_{18}$N$_4$O$_2$: Calculated: C,69.35;H,5.24;N, 16.17; Found:C,69.08;H,5.20;N,16.19%.

Analysis for $C_{26}H_{27}N_3O_3$: Calculated: C,72.71;H,6.34;N, 9.78; Found:C,72.53;H,6.39;N,9.53%. $[\alpha]_D^{20°}=+29.8°$ (C=1.07; $CHCl_3$).

EXAMPLE 87

(6R,12aR)-2,3,6,7,12,12a-Hexahydro-6-(3-chloro-4-ethoxyphenyl)-2-cyclopropylmethyl-pyrazino[2',1':6,1]pyrido[3,4-b]indole-1,4-dione The same two step procedure but starting from cyclopropylmethylamine and intermediate 59 gave, after recrystallisation from methanol, the title compound as white crystals m.p.: 218–219° C.

Analysis for $C_{25}H_{24}ClN_3O_3$ (0.25$H_2O$): Calculated: C,66.08;H,5.43;N,9.25;Cl,7.80; Found: C,66.11;H,5.33;N, 9.03;Cl,7.74%. $[\alpha]_D^{20°}=+49.4°$ (C=1.03; $CHCl_3$).

EXAMPLE 88

(6R,12aR)-2,3,6,7,12,12a-Hexahydro-2-cyclopentyl-6-3-chloro-4-methoxyphenyl)-pyrazino[2',1':6,1]pyrido[3,4-b]indole-1,4-dione The same two step procedure but starting from cyclopentylamine and intermediate 59 gave, after recrystallisation from methanol, the title compound as white crystals m.p.: 260–262° C.

Analysis for $C_{26}H_{26}ClN_3O_3$: Calculated: C,67.31;H, 5.65;Cl,7.64;N,9.06; Found:C,66.98;H,5.67;Cl,8.06;N, 9.04%. $[\alpha]_D^{20°}=+27.6°$ (C=1.05; $CHCl_3$).

EXAMPLE 89

(6R,12aR)-2,3,6,7,12,12a-Hexahydro-6-(3-chloro-4-methoxyphenyl)-2-methyl-pyrazino[2',1':6,1]pyrido[3,4b]indole-1,4-dione The same two step procedure but starting from methylamine and intermediate 59 gave, after recrystallisation from methanol, the title compound as white crystals m.p.: 283–284° C.

Analysis for $C_{22}H_{20}ClN_3O_3$: Calculated: C,64.47;H, 4.92;Cl,8.65;N,10.25; Found:C,64.49;H,4.92.Cl8.33.N, 10.02%. $[\alpha]_D^{20°}+=61.3°$ (C=1.00; $CHCl_3$).

EXAMPLE 90

(6R,12aR)-2,3,6,7,12,12a-Hexahydro-2-isopropyl-6-(3-chloro-4-methoxyphenyl)-pyrazino[2',1':6,1]pyrido[3,4-b]indole-1,4-dione The same two step procedure but starting from isopropylamine and intermediate 59 gave, after recrystallisation from methanol, the title compound as white crystals m.p.: 302–304° C.

Analysis for $C_{24}H_{24}ClN_3O_3$: Calculated: C,65.83;H, 5.52;N,9.60; Found:C,65.83;H,5.57.N,9.73%. $[\alpha]_D^{20°}=+39.8°$ (C=0.95; $CHCl_3$).

EXAMPLE 91

(6R,12aR)-2,3,6,7,12,12a-Hexahydro-6-(2,3-dihydrobenzo[b]furan-5-yl)-2-methyl-pyrazino[2',1':6.1]pyrido[3,4-b]indole-1,4-dione The same two step procedure but starting from methylamine and intermediate 61 gave, after recrystallisation from dichloromethane/methanol, the title compound as white crystals m.p.: 288–291° C.

Analysis for $C_{23}H_{21}N_3O_3$: Calculated: C,71.30;H,5.46;N, 10.85; Found:C,71.27;H,5.49;N,10.96%. $[\alpha]_D^{20°}=+65.6°$ (C=0.4; $CHCl_3$).

EXAMPLE 92

(6R,12aR)-2,3,6,7,12,12a-Hexahydro-6-(2,3-dihydrobenzo[b]furan-5-yl)-2-methylcyclopropyl-pyrazino[2',1':6,1]pyrido[3,4-b]indole-1,4-dione The same two step procedure but starting from methylcyclopropylamine and intermediate 61 gave, after recrystallisation from methanol, the title compound as white crystals m.p.: 242–244° C.

Analysis for $C_{26}H_{25}N_3O_3$: Calculated: C,73.05;H,5.89;N, 9.83; Found:C,72.90;H,5.93;N,9.98%. $[\alpha]_D^{20°}=+55.4°$ (C=0.99; $CHCl_3$).

EXAMPLE 93

(6R,12aR)-2,3,6,7,12,12a-Hexahydro-6-(5-indanyl)-2-methyl-pyrazino[2',1':6,1]pyrido[3,4-b]indole-1,4-dione The same two step procedure but starting from methylamine and intermediate 63 gave, after recrystallisation from methanol, the title compound as white crystals m.p. : 262° C.

Analysis for $C_{24}H_{23}N_3O_2$: Calculated: C,74.78;H,6.01;N, 10.90; Found:C,74.65;H,5.90;N,10.67%. $[\alpha]_D^{20°}=+68.6°$ (C=0.98; $CHCl_3$).

EXAMPLE 94

(6R,12aR)-2,3,6,7,12,12a-Hexahydro-6-(5-indanyl)-2-cyclopropylmethyl-pyrazino[2',1':6,1]pyrido[3,4-b]indole-1,4-dione The same two step procedure but starting from cyclopropylmethylamine and intermediate 63 gave, after recrystallisation from methanol, the title compound as white crystals m.p.: 176° C.

Analysis for $C_{27}H_{27}N_3O_2$ (0.25$H_2O$): Calculated: C,75.41;H,6.45;N,9.77; Found:C,75.25;H,6.51;N,9.75%. $[\alpha]_D^{20°}=+57.9°$ (C=1.00; $CHCl_3$).

EXAMPLE 95

(6R,12aR)-2,3,6,7,12,12a-Hexahydro-2-methyl-6-(3,4-methylenedioxyphenyl)-pyrazino[2',1':6,1]pyrido[3,4-b]indole-1,4-dione To a stirred suspension of Intermediate 73 (12.5 g) in MeOH (400 ml) was added at room temperature a solution of methylamine (33% in EtOH) (13.7 ml) and the resulting mixture was heated at 50° C. under $N_2$ for 14 hours. The solvent was removed under reduced pressure and the residue was dissolved in $CH_2Cl_2$ (1l). After washing with water (3×500 ml), drying over $Na_2SO_4$ and evaporating to dryness, the white solid obtained was recrystallised from 2-propanol to give the title compound as white needles (7.5 g). mp: 298–300° C. $[\alpha]_D^{20°}=+71.3°$ (c=0.55, $CHCl_3$). Elemental analysis ($C_{22}H_{19}N_3O_4$) calculated: C,67.86;H,4.92;N,10.79; found: C,67.79;H,4.95;N,10.61%.

EXAMPLE 96

Cis-2,3,6,7,12,12a-hexahydro-2,10-dimethyl-6-(3,4-methylenedioxyphenyl)-pyrazino[2',1':6.1]pyrido[3,4b]indole-1,4-dione The same two step procedure as used to prepare Example 1, but starting from methylamine and the cis isomer of Intermediate 74, gave after recrystallisation from ethanol, the title compound as white crystals m.p.: 275° C.

Analysis for $C_{23}H_{21}N_3O_4$ (0.4$H_2O$): Calculated: C,67.27;H,5.35;N,10.23; Found: C,67.36;H,5.21;N,10.31%.

EXAMPLE 97

(6R,12aR)-2,3,6,7,12,12a-Hexahydro-2-(3,4-dimethoxybenzyl)-6-(3,4-methylenedioxyphenyl)-pyrazino[2',1':6,1]pyrido[3,4b]indole-1,4-dione The same two step procedure as used to prepare Example 78, but starting from veratrylamine and intermediate 54 gave, after recrystallisation from methanol, the title compound as white crystals m.p.: 224226° C.

Analysis for $C_{30}H_{27}N_3O_6$: Calculated: C,68.56;H,5.18;N, 8.00; Found: C,68.80;H,5.11;N,8.06%. $[\alpha]_D^{20°}$+43.9° (C=1.02; $CHCl_3$).

EXAMPLE 98

Cis-2,3,6,7,12,12a-hexahydro-6-(4-aminophenyl)-2-butyl-pyrazino[2',1':6,1]pyrido[3,4-b]indole-1,4-dione To a solution of Example 75 (1.5 g) in methanol (100 mL) was added $SnCl_2.H_2O$ (3.06) and the resulting mixture was heated at reflux for 8 hours. The mixture was cooled to ambient temperature, poured into ice and was adjusted to pH5 with 1N NaOH. The methanol was evaporated off and the residue was basified to pH11 with 1N NaOH and extracted with EtOAc (2×150 mL). After drying over $Na_2SO_4$ and evaporation of EtOAc, the resulting yellow powder was purified by radial chromatography eluting with $CH_2Cl_2$ to give the title compound as a white powder (550 mg) m.p.: 192° C.

Analysis for $C_{24}H_{26}N_4O_2$ (1.3 $H_2O$): Calculated: C,67.68;H,6.77;N,13.15; Found: C,67.74;H,6.68;N,13.02%.

EXAMPLE 99

Cis-2,3,6,7,12,12a-hexahydro-6-(4-acetamidophenyl)-2-butyl-pyrazino[2',1':6,1]pyrido[3,4b]indole-1,4-dione To a solution of Example 98 (0.2 g) in THF (15 mL) was added triethylamine (76 μl) and acetyl chloride (39 μl) and the resulting solution was stirred at room temperature for 2 hours. After evaporation of THF, the resulting residue was taken up in $CH_2Cl_2$ (100 mL), washed with water (2×50 mL) and dried over $Na_2SO_4$. After evaporation of $CH_2Cl2$, the resulting solid was recrystallised from MeOH/$H_2O$ to give the title compound as a cream powder (120 mg) m.p.: 246° C.

Analysis for $C_{26}H_{28}N_4O_3$: Calculated: C,70.25;H,6.35;N, 12.60; Found: C,69.85;H,6.38;N,12.56%.

EXAMPLE 100

Cis-2,3,6,7,12,12a-hexahydro-2-butyl-6-(4-methylsulfonamidophenyl)-pyrazino[2',1':6,1]pyrido[3,4-b]indole-1,4-dione To a solution of Example 98 (0.2 g) in THF (5 mL) was added triethylamine (228 μL) and methanesulfonyl chloride (126 μL) and the solution was heated at reflux for 6 hours. After evaporation of THF, the residue was taken up in $CH_2Cl_2$, washed with water and dried over $Na_2SO_4$. After evaporation of $CH_2Cl_2$, the residue was purified by radial chromatography eluting with $CH_2Cl_2$/MeOH (95/5) to give the title compound as a brown powder (30 mg) m.p.: 188° C.

Analysis for $C_{25}H_{28}N_4O_4S$ (0.75$H_2O$): Calculated: C,60.77;H,6.02;N,11.34; Found: C,60.61;H,6.02;N,10.82%.

EXAMPLE 101

(6R,12aR)-2,3,6,7,12,12a-Hexahydro-6-(3,4-methylenedioxyphenyl)-pyrazino[2',1':6.1]pyrido[3,4-b]indole-1,4-dione The same two step procedure but starting from ammonia and intermediate 54 gave, after recrystallisation from methanol, the title compound as white crystals m.p.: 285–290° C.

Analysis for $C_{21}H_{17}N_3O_4$: Calculated: C,67.19;H,4.56;N, 11.19; Found: C,67.30;H,4.66;N,11.11%. $[\alpha]_D^{20°}$=+88° (c=0.48; pyridine).

EXAMPLE 102

(6R,12aR)-2,3,6,7,12,12a-Hexahydro-6-(3,4-methylenedioxyphenyl)-2-(2-propynyl)-pyrazino[2',1':6,1]pyrido[3,4-b]indole-1,4-dione The same two step procedure but starting from propargylamine and intermediate 54 gave, after recrystallisation from acetone, the title compound as white crystals m.p.: 271° C.

Analysis for $C_{24}H_{19}N_3O_4$: Calculated: C,69.72;H,4.63;N, 10.16; Found: C,69.95;H,4.66;N,10.06%. $[\alpha]_D^{20°}$=+51.7° (c=0.49; $CHCl_3$).

EXAMPLE 103

(6R,12aR)-2,3,6,7,12,12a-Hexahydro-2-(3,4-methylendioxybenzyl)-6-3,4-methylenedioxyphenyl)-pyrazino[2',1':6.1]pyrido[3,4-b]indole-1,4-dione The same two step procedure but starting from piperonylamine and intermediate 54 gave, after recrystallisation from methanol, the title compound as white crystals m.p.: 204–206° C.

Analysis for $C_{29}H_{23}N_3O_6$: Calculated: C,68.36;H,4.55;N, 8.25; Found: C,68.25;H,4.49;N,8.41. $[\alpha]_D^{20°}$=+43° (c=1.01; $CHCl_3$).

EXAMPLE 104

(6R,12aR)-2,3,6,7,12,12a-Hexahydro-2-(3,4-dimethoxyphenethyl)-6-3.4-methylenedioxyphenyl)-pyrazino[2',1':6,1]pyrido[3,4-b]indole-1,4-dione The same two step procedure but starting from 3,4-dimethoxyphenethylamine and intermediate 54 gave, after recrystallisation from dichloromethane/ether, the title compound as white crystals m.p.: 265–266° C.

Analysis for $C_{31}H_{29}N_3O_6$: Calculated: C,69.00;H,5,42;N, 7.79; Found: C,68.68;H,5.35;N,7.78%. $[\alpha]_D^{20°}$=+38.3° (c=1.12; $CHCl_3$).

EXAMPLE 105

(6R,12aR)-2,3,6,7,12,12a-hexahydro-2-furfuryl-6-(3,4-methylenedioxyphenyl)-pyrazino[2',1':6,1]pyrido[3,4-b]indole-1,4-dione The same two step procedure but starting from furfurylamine and intermediate 54 gave, after recrystallisation from methanol, the title compound as white crystals m.p.: 219° C.

Analysis for $C_{26}H_{21}N_3O_5$: Calculated: C,68.56;H,4.65;N, 9.23; Found: C,68.16;H,4.63;N,9.15%. $[\alpha]_D^{20°}$=+58.1° (C=1.2; $CHCl_3$)

EXAMPLE 106

(6R,12aR)-2,3,6,7,12,12a-Hexahydro-6-(3,4-methylenedioxyphenyl)-2-(2-thienylmethyl)-pyrazino[2',1':6,1]pyrido[3,4-b]indole-1,4-dione The same two step procedure but starting from 2-thiophenemethylamine and intermediate 54 gave, after recrystallisation from methanol/water, the title compound as white crystals m.p.: 155–157° C.

Analysis for $C_{26}H_{21}N_3O_4S$: Calculated: C,66.23;H,4.49;N,8.91S,6.8; Found: C,66.13;H,4.54;N,9.12;S,6.78%. $[\alpha]_D^{20°}=+70.4°$ (c=1.03; CHCl$_3$).

EXAMPLE 107

(6R,12aR)-2,3,6,7,12,12a-Hexahydro-6-(4-methoxyphenyl)-2-methyl-pyrazino[2',1':6,1]pyrido[3,4-b]indole-1,4-dione The same two step procedure but starting from methylamine and intermediate 57 gave, after recrystallisation from methanol, the title compound as white crystals m.p.: 285–288° C.

Analysis for $C_{22}H_{21}N_3O_3$: Calculated: C,70.38;H,5.64;N,11.19; Found: C,70.31;H,5.69;N,11.29%. $[\alpha]_D^{20°}=+59°$ (c=1.19; CHCl$_3$).

EXAMPLE 108

(6R,12aR)-2,3,6,7,12,12a-Hexahydro-2-ethyl-6-(4-methoxyphenyl)-pyrazino[2',1':6,1]pyrido[3,4-b]indole-1,4-dione The same two step procedure but starting from ethylamine and intermediate 57 gave, after recrystallisation from methanol, the title compound as white crystals m.p.: 277° C.

Analysis for $C_{23}H_{23}N_3O_3$: Calculated: C,70.93;H,5.95;N,10.79; Found: C,70.90;H,5.96;N,10.54%. $[\alpha]_D^{20°}=+52°$ (c=1.28; CHCl$_3$).

EXAMPLE 109

(6R,12aR)-2,3,6,7,12,12a-hexahydro-6-(7-(4-methyl-3,4-dihydro-2H-benzo[1.4]oxazinyl))-2-methyl-pyrazino[2',1':6,1]pyrido[3,4-b]indole-1,4-dione The same two step procedure but starting from intermediate 75 and methylamine gave, after recrystallisation from ethanol, the title compound as white crystals m.p.: 285–288° C.

Analysis for $C_{24}H_{24}N_4O_3$ (0.5H$_2$O): Calculated: C,67.75;H,5.92;N,13.17; Found:C,68.02;H,6.00;N,13.18%. $[\alpha]_D^{20°}+71.7°$ (c=1, pyridine).

EXAMPLE 110

(6R,12aR)-2,3,6,7,12,12a-Hexahydro-6-(5-(N-benzylindolinyl))-2-methyl-pyrazino[2',1':6.1]pyrido[3,4-b]indole-1,4-dione The same two step procedure but starting from intermediate 77 and methylamine gave, after recrystallisation from dichloromethane/methanol, the title compound as white crystals m.p.: 223–225° C.

Analysis for $C_{30}H_{28}N_4O_2$: Calculated: C,75.61;H,5.92;N,11.76; Found: C,75.2;H,5.78;N,11.67%. $[\alpha]_D^{20°}=+20.4°$ (c=0.5, CHCl$_3$).

EXAMPLE 111

(6R,12aR)-2,3,6,7,12,12a-Hexahydro-6-(5-indolinyl)-2-methyl-pyrazino[2',1':6,1]pyrido[3,4-b]indole-1,4-dione A solution of Example 110 (1.05 g, 2.2 mmol) in methanol (100 mL) was hydrogenated in the presence of 10% Pd-C (100 mg) for 48 hours at room temperature. After removal of the catalyst, the solvent was evaporated in vacuo to leave a residue which was purified by flash chromatography eluting with dichloromethane/methanol: 9614. The solid obtained was recrystallised from dichloromethane/methanol to give the title compound (300 mg) as white crystals m.p.: 240° C.

Analysis for $C_{23}H_{22}N_4O_2$ (0.5H$_2$O): Calculated: C,69.86;H,5.86;N,14.17; Found: C,70.13;H,5.77;N,14.06%. $[\alpha]_D^{20°}=+55.9°$ (c=1.18; pyridine).

EXAMPLE 112

Cis-2,3,6,7,12,12a-hexahydro-6-(4-ethylphenyl)-2-methyl-pyrazino[2',1':6,1]pyrido[3,4b]indole-1,4-dione The same two step procedure but starting from methylamine and the cis isomer of intermediate 42 gave, after recrystallisation from methanol, the title compound as white crystals m.p.: 254° C.

Analysis for $C_{23}H_{23}N_3O_2$ (0.25H$_2$O): Calculated: C,73.09;H,6.27;N,11.12; Found: C,73.03;H,6.18;N,11.36%.

EXAMPLE 113

(6R,12aR)-2,3,6,7,12,12a-Hexahydro-6-(4-carbomethoxyphenyl)-2-methyl-pyrazino[2',1':6,1]pyrido[3,4-b]indole-1,4-dione The same two step procedure but starting from intermediate 78 (cis isomer) and methylamine gave, after recrystallisation from methanol, the title compound as white crystals m.p.: 308–312° C.

Analysis for $C_{23}H_{21}N_3O_4$: Calculated: C,68.47;H,5.25;N,10.42; Found: C,68.76;H,5.18;N,10.35%. $[\alpha]_D^{20°}=+97.7°$ (c=1, pyridine).

EXAMPLE 114

(5aR,12R,14aR)-1,2,3,5a,6,11,12,14a-Octahydro-12-(3,4-methylenedioxyphenyl)-pyrrolo[1",2":4',5']pyrazino[2',1':6,1]pyrido[3,4-b]indole-5-1,4-dione A solution of intermediate 80 (0.7 g, 1.2 mmol) in a mixture of methanol/THF (80/40 mL) was hydrogenated in the presence of 10% Pd-C (75 mg) for 48 hours at 40° C. After removal of the catalyst, the solvent was evaporated in vacuo to leave a residue, which was purified by flash chromatography eluting with dichloromethane/methanol: 9812. The white solid obtained was recrystallised from methanol to give the title compound (180 mg) as white crystals m.p.: 284–287° C.

Analysis for $C_{24}H_{21}N_3O_4$: Calculated: C,69.39;H,5.10;N,10.11; Found: C,69.47;H,5.11;N,9.97%. $[\alpha]_D^{20°}=+21.7°$ (c=0.64, CHCl$_3$).

EXAMPLE 115

(5aR,12R,14aS)-1,2,3,5,6,11,12,14a-Octahydro-12-(3,4-methylenedioxyphenyl)-pyrrolo[1",2":4',5']pyrazino[2',1':6,1]pyrido[3,4-b]indole-5-1,4-dione A solution of intermediate 81 (0.8 g, 1.37 mmol) in methanol (40 mL) was hydrogenated in the presence of 10% Pd-C (100 mg) for 5 h at 45° C. After removal of the catalyst the solvent was evaporated in vacuo to leave a residue, which was purified by flash chromatography eluting with dichloromethane/methanol: 9812. The solid obtained was recrystallised from methanol to give the title compound (300 mg) as white crystals m.p.: 302–304° C.

Analysis for $C_{24}H_{21}N_3O_4$: Calculated: C,69.39;H,5.10;N,10.11; Found: C,69.35;H,5.11;N,10.10%. $[\alpha]_D^{20°}=+106.8°$ (c=1.08, CHCl$_3$).

EXAMPLE 116

(3R,6R,12aR)-2,3,6,7,12,12a-hexahydro-2,3-dimethyl-6-(3,4-methylenedioxyphenyl)-pyrazino[2',1':6,1]pyrido[3,4-b]indole-1,4-dione To a stirred solution of intermediate 82 (0.15 g, 0.34 mmol) in THF (15 mL) was added at room temperature a solution of methylamine (33% in EtOH) (0.32 mL) and the resulting solution was heated at reflux under $N_2$ for 24 hours. The solvent was removed under reduced pressure and the residue was dissolved in $CH_2Cl_2$ (25 mL). After washing with water (2×20 mL), drying over $Na_2SO_4$ and evaporating to dryness, the crude product was purified by flash chromatography eluting with dichloromethane/methanol: 99/1. The white solid obtained was recrystallised from methanol to give the title compound as white crystals (80 mg) m.p.: 219–220° C.

Analysis for $C_{23}H_{21}N_3O_4$: Calculated: C,68.47;H,5.25;N,10.42; Found: C,68.39;H,5.21;N,10.42%. $[\alpha]_D^{20°}=+89.6°$ (c=1; $CHCl_3$).

EXAMPLE 117

(3S,6R,12aR)-2,3,6,7,12,12a-hexahydro-2,3-dimethyl-6-(3,4-methylenedioxyphenyl)-pyrazino[2',1':6,1]pyrido[3,4-b]indole-1,4-dione To a stirred solution of intermediate 83 (0.3 g, 0.68 mmol) in THF (30 mL) was added at room temperature a solution of methylamine (33% in EtOH) (0.68 mL) and the resulting solution was treated at reflux under $N_2$ for 6 days. The solvent was removed under reduced pressure and the residue was dissolved in $CH_2Cl_2$ (50 mL). After washing with water (2,25 mL), drying over $Na_2SO_4$ and evaporating to dryness, the crude product was purified by flash chromatography eluting with dichloromethane/methanol: 99/1. The oily residue obtained was crystallised from methanol to give the title compound as white crystals (40 mg) m.p.: 307–309° C.

Analysis for $C_{23}H_{21}N_3O_4$: Calculated: C,68.47;H,5.25;N,10.42; Found: C,68.35;H,5.33;N,10.42%. $[\alpha]_D^{20°}=+65.2°$ (c=1.15; $CHCl_3$).

EXAMPLE 118

(6R,12aR)-2,3,6,7,12,12a-Hexahydro-6-3,4-hydroxyphenyl)-2-methyl-pyrazino[2',1':6,1]pyrido[3,4-b]indole-1,4-dione A solution of intermediate 86 (0.75 g; 1.34 mmol) in a mixture of ethanol/THF (70/30 mL) was hydrogenated in the presence of 10% Pd-C (75 mg) for 24 h at room temperature. After removal of the catalyst, the solvent was evaporated in vacuo to leave a white solid which was recrystallisated from methanol to give the title compound (0.35 g) as white crystals m.p.: 224–226° C.

Analysis for $C_{21}H_{19}N_3O_4$: Calculated: C,66.83;H,5.07;N,11.13; Found: C,66.58;H,5.01;N,11.04%. $[\alpha]_D^{20°}=+58.4°$ (c=1.04; pyridine).

EXAMPLE 119

(6R,12aR)-2,3,6,7,12,12a-Hexahydro-2-methyl-6-(5-(2-methylisoindolinyl))pyrazino[2',1':6,1]pyrido[3,4b]indole-1,4-dione The same two steps procedure but starting from intermediate 87 and methylamine gave a crude oil which was purified by flash chromatography eluting with dichloromethane/methanol/triethylamine: 92/810.1%. The solid obtained was recrystallized from isopropanolpropyl ether/water to give the title compound (20 mg) as off-white crystals m.p.: 236° C.

Analysis for $C_{24}H_{24}N_4O_2$ (2.68$H_2O$) Calculated: C,64.23;H,6.59;N,12.48; Found: C,64.21;H,6.43;N,12.02%. $[\alpha]_D^{20°}=+61.1°$ (c=0.5; $CH_3OH$).

EXAMPLE 120

Compounds of formula (I) have been included in pharmacy formulations and details of such formulations are given below.

TABLETS FOR ORAL ADMINISTRATION

A. Direct Compression

| 1. | mg/tablet |
| --- | --- |
| Active ingredient | 50.0 |
| Crospovidone USNF | 8.0 |
| Magnesium Stearate Ph Eur | 1.0 |
| Anhydrous Lactose | 141.0 |

The active ingredient was sieved and blended with the excipients. The resultant mix was compressed into tablets.

| 2. | mg/tablet |
| --- | --- |
| Active ingredient | 50.0 |
| Colloidal Silicon Dioxide | 0.5 |
| Crospovidone | 8.0 |
| Sodium Lauryl Sulphate | 1.0 |
| Magnesium Stearate Ph Eur | 1.0 |
| Microcrystalline Cellulose USNF | 139.5 |

The active ingredient was sieved and blended with the excipients. The resultant mix was compressed into tablets.

B. Wet Granulation

| 1. | mg/tablet |
| --- | --- |
| Active ingredient | 50.0 |
| Polyvinyl pyrollidone | 150.0 |
| Polyethylene glycol | 50.0 |
| Polysorbate 80 | 10.0 |
| Magnesium Stearate Ph Eur | 2.5 |
| Croscarmellose Sodium | 25.0 |
| Colloidal Silicon Dioxide | 2.5 |
| Microcrystalline Cellulose USNF | 210.0 |

The polyvinyl pyrollidone, polyethylene glycol and polysorbate 80 were dissolved in water. The resultant solution was used to granulate the active ingredient. After drying the granules were screened, then extruded at elevated temperatures and pressures. The extrudate was milled and/or screened then was blended with the microcrystalline cellulose, croscarmellose sodium, colloidal silicon dioxide and magnesium stearate. The resultant mix was compressed into tablets.

| 2. | mg/tablet |
| --- | --- |
| Active ingredient | 50.0 |
| Polysorbate 80 | 3.0 |
| Lactose Ph Eur | 178.0 |

-continued

| 2. | mg/tablet |
|---|---|
| Starch BP | 45.0 |
| Pregelatinised Maize Starch BP | 22.5 |
| Magnesium Stearate BP | 1.5 |

The active ingredient was sieved and blended with the lactose, starch and pregelatinised maize starch. The polysorbate 80 was dissolved in purified water. Suitable volumes of the polysorbate 80 solution were added and the powders were granulated. After drying, the granules were screened and blended with the magnesium stearate. The granules were then compressed into tablets.

Tablets of other strengths may be prepared by altering the ratio of active ingredient to the other excipients.

FILM COATED TABLETS

The aforementioned tablet formulations were film coated.

| Coating Suspension | % w/w |
|---|---|
| Opadry white† | 13.2 |
| Purified water Ph Eur | to 100.0* |

*The water did not appear in the final product. The maximum theoretical weight of solids applied during coating was 20 mg/tablet.
†Opadry white is a proprietary material obtainable from Colorcon Limited, UK which contains hydroxypropyl methylcellulose, titanium dioxide and triacetin.

The tablets were film coated using the coating suspension in conventional film coating equipment.

CAPSULES

| 1. | mg/capsule |
|---|---|
| Active ingredient | 50.0 |
| Lactose | 148.5 |
| Polyvinyl pyrollidone | 100.0 |
| Magnesium Stearate | 1.5 |

The active ingredient was sieved and blended with the excipients. The mix was filled into size No. 1 hard gelatin capsules using suitable equipment.

| 2. | mg/capsule |
|---|---|
| Active ingredient | 50.0 |
| Microcrystalline Cellulose | 233.5 |
| Sodium Lauryl Sulphate | 3.0 |
| Crospovidone | 12.0 |
| Magnesium Stearate | 1.5 |

The active ingredient was sieved and blended with the excipients. The mix was filled into size No. 1 hard gelatin capsules using suitable equipment Other doses may be prepared by altering the ratio of active ingredient to excipient, the fill weight and if necessary changing the capsule size.

| 3. | mg/capsule |
|---|---|
| Active ingredient | 50.0 |
| Labrafil M1944CS | to 1.0 ml |

The active ingredient was sieved and blended with the Labrafil. The suspension was filled into soft gelatin capsules using appropriate equipment.

EXAMPLE 121

Inhibitory effect on cGMP-PDE cGMP-PDE activity of compounds of the present invention was measured using a one-step assay adapted from Wells at al. (Wells, J. N., Baird, C. E., Wu, Y. J. and Hardman, J. G., Biochim. Biophys. Acta 384, 430 (1975)). The reaction medium contained 50 mM Tris-HCl,pH 7.5, 5mM Mg-acetate, 250µg/ml 5'-Nucleotidase, 1 mM EGTA and 0.15 µM 8-[H$^3$]-cGMP. The enzyme used was a human recombinant PDE V (ICOS, Seattle USA).

Compounds of the invention were dissolved in DMSO finally present at 2% in the assay. The incubation time was 30 minutes during which the total substrate conversion did not exceed 30%.

The IC$_{50}$ values for the compounds examined were determined from concentration-response curves using typically concentrations ranging from 10 nM to 10 µM. Tests against other PDE enzymes using standard methodology also showed that compounds of the invention are highly selective for the cGMP specific PDE enzyme.

-cGMP level measurements

Rat aortic smooth muscle cells (RSMC) prepared according to Chamley et al. in Cell Tissue Res. 177 503–522 (1977) were used between the 10th and 25th passage at confluence in 24-well culture dishes. Culture media was aspirated and replaced with PBS (0.5 ml) containing the compound tested at the appropriate concentration. After 30 minutes at 37° C., particulates guanylate cyclase was stimulated by addition of ANF (100 nM) for 10 minutes. At the end of incubation, the medium was withdrawn and two extractions were performed by addition of 65% ethanol (0.25 ml). The two ethanolic extracts were pooled and evaporated until dryness, using a Speed-vac system. c-GMP was measured after acetylation by scintillation proximity immunoassay (AMERSHAM).

The compounds according to the present invention were typically found to exhibit an IC$_{50}$ value of less than 500 nM, and an EC$_{50}$ value of less than 5. In vitro test data for representative compounds of the invention is given in following Table 1:

TABLE 1

| Example No. | IC$_{50}$ nM | EC$_{50}$ µM |
|---|---|---|
| 12 | 10 | 0.15 |
| 36 | <10 | 0.5 |
| 52 | 20 | 0.8 |
| 63 | 30 | 0.35 |
| 79 | <10 | 0.15 |
| 82 | 20 | 0.5 |
| 84 | 10 | 0.4 |
| 89 | 10 | <0.1 |
| 95 | 2 | 0.2 |
| 101 | 10 | 0.3 |

TABLE 1-continued

| Example No. | IC$_{50}$ nM | EC$_{50}$ µM |
|---|---|---|
| 115 | <10 | 0.4 |

EXAMPLE 122

Antihypertensive activity in rats

The hypotensive effects of compounds according to the invention as identified in table 2 were studied in conscious spontaneously hypertensive rats (SHR). The compounds were administered orally at a dose of 5 mg/kg in a mixture of 5% DMF and 95% olive oil. Blood pressure was measured from a catheter inserted in the carotid artery and recorded for 5 hours after administration. The results are expressed as Area Under the Curve (AUC from 0 to 5 hours, mmHg.hour) of the fall in blood pressure over time.

In Vivo Results

| Example No. | AUC PO (mmHg.h) |
|---|---|
| 36 | 99 |
| 63 | 95 |
| 79 | 171 |
| 82 | 111 |
| 84 | 77 |
| 89 | 117 |

| Example No. | AUC PO (mmHg.h) |
|---|---|
| 95 | 135 |
| 101 | 136 |

What is claimed is:

1. Compounds of formulae

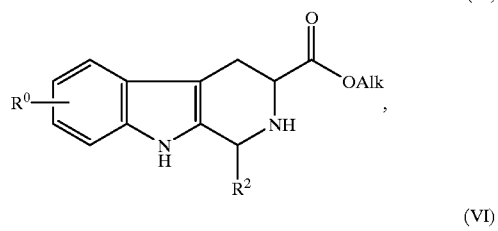
(III)

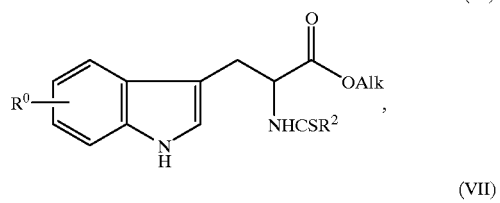
(VI)

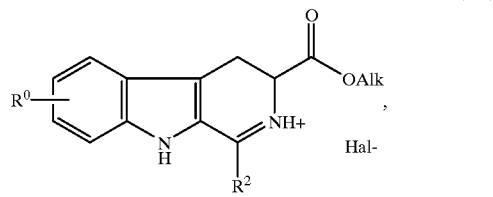
(VII)

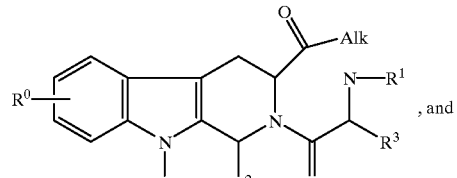
, and (VIII)

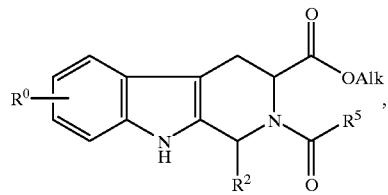
(X)

wherein Alk represents $C_{1-6}$alkyl;

Hal represents a halogen atom;

$R^0$ represents hydrogen, halogen, or $C_{1-6}$alkyl;

$R^1$ represents hydrogen, $C_{1-6}$alkyl, $C_{2-6}$alkenyl, $C_{2-6}$alkynyl, halo$C_{1-6}$alkyl, $C_{3-8}$cycloalkyl, $C_{3-8}$cycloalkyl-$C_{1-3}$alkyl, aryl$C_{1-3}$alkyl, or heteroaryl$C_{1-3}$alkyl;

$R^2$ represents an optionally substituted monocyclic aromatic ring selected from benzene, thiophene, furan, and pyridine, or an optionally substituted bicyclic ring

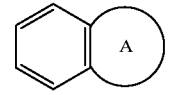

attached to the rest of the molecule via one of the benzene ring carbon atoms and wherein the fused ring A is a 5- or 6-membered ring which may be saturated or partially or fully unsaturated and comprises carbon atoms and optionally one or two heteroatoms selected from oxygen, sulphur, and nitrogen, and $R^3$ represents hydrogen or $C_{1-3}$alkyl, or $R^1$ and $R^3$ together represent a 3- or 4-membered alkyl or alkenyl chain; and $R^5$ represents $C_2$–$C_5$alkyl, substituted at C, by a halogen atom, with the exception for compounds (III), (VI), and (VII) wherein $R^0$ is hydrogen, $R^2$ is phenyl, and Alk is methyl.

2. A compound of formula

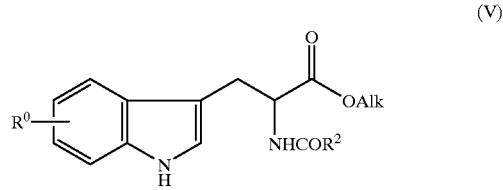
(V)

wherein Alk represents $C_{1-6}$alkyl;

$R^0$ represents hydrogen, halogen, or $C_{1-6}$alkyl;

$R^2$ represents an optionally substituted monocyclic aromatic ring selected from thiophene, furan, and pyridine.

* * * * *

UNITED STATES PATENT AND TRADEMARK OFFICE
CERTIFICATE OF CORRECTION

PATENT NO. : 6,127,542
DATED : October 3, 2000
INVENTOR(S) : Daugan

It is certified that error appears in the above-identified patent and that said Letters Patent is hereby corrected as shown below:

Title page,
Item [30], Foreign Application Priority Data, "940109.7" should be -- 9401090.7 --
Item [56], References Cited, OTHER PUBLICATIONS, third reference, "DelLouve-Courillon" should be -- Dellouve-Courillon --
Item [57], ABSTRACT,
Line 25, "$C_{3-8}$cyloalkyl," should be -- $C_{3-8}$cycloalkyl, --
Line 49, "3',5'-mnonophosphate" should be -- 3'5'-monophosphate --

Column 2,
Line 29, "to which may be saturated" should be -- which may be saturated --
Line 44, "C3-6cycloalkyl" should be -- $C_{3-6}$cycloalkyl Column 4,
Line 61, "4dione;" should be -- 4-dione; --
Line 63, "[3,4b]" should be -- [3,4-b] --

Column 5,
Lines 2, 9 and 12, "[3,4b]" should be -- [3,4-b] --
Line 16, "-methyl6-" should be -- -methyl-6- --
Line 64, "a compound of formula (I)," should be -- 'a compound of formula (I),' --

Column 7,
Line 5, "PEG6" should be -- PEG-6 --

Column 8,
Lines 60-61, "in one a step." should be -- in one step. --

Column 10,
Line 47, "(VII)" should be -- (VIII) --

Column 12,
Line 44, "1-3-methoxyphenyl)" should be -- 1-(3-methoxyphenyl) --
Line 62, "-1-2,3-dihydrobenzo" should be -- -1-(2,3-dihydrobenzo --

Column 13,
Line 32, "m.p.208-209°C." should be -- m.p.:208-209°C --
Line 46, "2.9(m, 1H-4);" should be -- 2.9 (m, 1H, H-4); --
Line 52, "naphthyl)9H" should be -- naphthyl)-9H --
Lines 59-60, "2.7 (m, 4H, $CH_2Ar$); 1.7 (s, 4H, $CH_2CH_2Ar$)." should be -- 2.7 (m, 4H, $CH_2Ar$); 1.7 (s, 4H, $CH_2Ar$). --

UNITED STATES PATENT AND TRADEMARK OFFICE
CERTIFICATE OF CORRECTION

PATENT NO. : 6,127,542
DATED : October 3, 2000
INVENTOR(S) : Daugan

It is certified that error appears in the above-identified patent and that said Letters Patent is hereby corrected as shown below:

Column 14,
Line 29, "tetrahydrol-" should be -- tetrahydro-1- --

Column 15,
Line 10, "[3,4b]" should be -- [3,4-b] --

Column 16,
Line 33, "-Me)$_2$)" should be -- -(ME)$_2$) --
Line 37, "4nitrophenyl" should be -- 4-nitrophenyl --
Line 48, "[3,4b]" should be -- [3,4-b] --

Column 17,
Lines 17-18, "indole-carboxylate," should be -- indole-3-carboxylate, --
Line 63, "methoxyphenyl) 9H-" should be -- methoxyphenyl)-9H --

Column 18,
Line 10, "[b]furan))-" should be -- [b]furan)- --

Column 20,
Line 11, "(9.289)" should be -- (9.28g) --
Line 51, "2chloroacetyl" should be -- 2-chloroacetyl --

Column 21,
Line 2, "dropwide" should be -- dropwise --
Lines 25 and 28, "[1.4]" should be -- [1,4] --
Line 51, "(4carboheptoxyphenyl)" should be -- (4-carbomethoxyphenyl) --

Column 22,
Line 2, "0.33 m" should be -- 0.33 mL --
Line 10, "(0.75 9)" should be -- (0.75 g) -
Line 19, "(0.91 g. 2.6 mmol)" should be -- (0.91 g, 2.6 mmol) --
Line 26, "menthol/water" should be -- methanol/water --
Line 46, "1-3,4-methylenedioxypphenyl)" should be -- -1-(3,4-methylenedioxyphenyl) --
Line 62, "4dibenzyloxypphenyl)" should be -- 4-dibenzyloxyphenyl) --
Line 64, "-1-3,4-dibenzyloxyphenyl)" should be -- -1-(3,4-dibenzyloxyphenyl) --

Column 23,
Lines 12 and 63, "[2',1':6.1]" should be -- [2',1':6,1]--
Line 31, "indole-14-dione" should be -- indole-1,4-dione --

UNITED STATES PATENT AND TRADEMARK OFFICE
CERTIFICATE OF CORRECTION

PATENT NO.   : 6,127,542
DATED        : October 3, 2000
INVENTOR(S)  : Daugan

It is certified that error appears in the above-identified patent and that said Letters Patent is hereby corrected as shown below:

Column 24,
Lines 6, 30 and 40, "[2',1':6.1]" should be -- [2',1':6,1] --
Lines 51-52 and 62-63, "[2',1':6.1]pyrido[3,4b]" should be -- [2',1':6,7.]pyrido[3,4-b] --

Column 25,
Line 2, "C,69.56," should be -- C, 69.56; --
Line 7, "-6-3,4-methylenedioxyphenyl)pyrazino" should be -- -6-(3,4-methylenedioxyphenyl)-pyrazino --
Line 10, "2,2pyridyl)" should be -- 2-(2-pyridyl) --
Line 27, "-2-3-pyridylmethyl)" should be -- -2-(3-pyridylmethyl) --
Line 50, "-2-methyl-6-" should be -- -2-ethyl-6- -

Column 26,
Lines 18-19 and 30-31, "[3,4b]" should be -- [3,4-b] -
Line 37, "C,69.1;" should be -- C, 69.11; --

Column 27,
Line 26, "menthol/water" should be -- methanol/water --
Line 48,"[3,4b]"should be -- [3,4-b] --

Column 28,
Lines 16 and 52, "[3,4b]" shouldbe -- [3,4-b] --

Column 29,
Lines 34 and 47, "[3,4b]" shouldbe -- [3,4-b] --

Column 30,
Line 4, "furan-5-yl-2" should be -- furan-5-yl)-2- --
Line 38, "12,1 2a-hexahydro" should be -- 12,12a-hexahydro --
Lines 46 and 57, "ClN$_3$" should be -- ClN$_3$ --
Line 50, "-6-chlorophenyl)-" should be -- -6-(4-chlorophenyl)- --

Column 31,
Line 1, "ClN$_3$" should be -- ClN$_3$ --
Line 7, "(4-dichlorophenyl)" should be -- (3,4-dichlorophenyl) --
Line 19, "-2-butylphenyl-" should be -- -2-butyl-6-phenyl- --

UNITED STATES PATENT AND TRADEMARK OFFICE
CERTIFICATE OF CORRECTION

PATENT NO.   : 6,127,542
DATED        : October 3, 2000
INVENTOR(S)  : Daugan

Page 4 of 6

It is certified that error appears in the above-identified patent and that said Letters Patent is hereby corrected as shown below:

Column 32,
Line 22, "$C_28H_{29}N_3O_2$" should be -- $C_{28}H_{29}N_3O_1$ --

Column 33,
Lines 30 and 42, "[3,4b]" should be -- [3,4-b] -
Line 48, "$C_{19}H_17N_2O_2S$" should be -- $C_{19}H_{17}N_3O_2S$ --

Column 34,
Line 26, "N, 1.59%." should be -- N, 11.59%. --
Line 50, "12,1 2a-hexahydro" should be --12,12a-hexahydro --
Line 51, "[3,4b]" should be -- [3,4-b] --

Column 35,
Line 62, "[3,4b]" should be -- [3,4-b] --

Column 36,
Lines 6, 52 and 62, "[3,4b]" should be -- [3,4-b] --
Line 40, "[2',1':6.1]" should be -- [2',1':6,1] --

Column 37,
Line 17, "1-1( 3,4-methylenedioxyphenyl)" should be -- -1-(3,4-methylenedioxyphenyl) --
Line 28, "(9911)" should be -- (99/1) --
Line 51, "[3,4b]" should be -- [3,4-b] --

Column38,
Line 26, "2propanol" should be -- 2-propanol --
Line36, "[3,4b]" should be -- [3,4-b] --
Line 48, "[3,4b]" should be -- [3,4-b] --

Column39,
Line7, "ethoxyphenyl" should be -- methoxyphenyl --
Lines14, 27, 39, and 53 "$ClN_3$" should be -- $ClN_3$ --
Line 20, "-6-3-chloro-4" should be -- -6-(3-chloro-4 --
Line 34, "[3,4b]" should be -- [3,4-b] --
Line 41, "C, 64.49; H,4.92.C18.33.N,10.02%." should be-- C, 64.49; H, 4.92; Cl, 8.33; N, 10.02%. --
Lines 59-60, "[2',1':6.1]" should be -- [2',1':6,1]--

Column 40,
Lines 62-63, "[2',1':6.1]pyrido[3,4b]" should be -- [2',1':6,1]pyrido[3,4-b] --

UNITED STATES PATENT AND TRADEMARK OFFICE
CERTIFICATE OF CORRECTION

PATENT NO. : 6,127,542
DATED : October 3, 2000
INVENTOR(S) : Daugan

It is certified that error appears in the above-identified patent and that said Letters Patent is hereby corrected as shown below:

Column 41,
Lines 8 and 39, "[3,4b]" should be -- [3,4-b] --
Line 12, "224226°C." should be -- 224-226°C. --

Column 42,
Lines 28-29, "-6-3,4-methylenedioxyphenyl)-pyrazino[2',1':6.1]" should
be -- -6-(3,4-methylenedioxyphenyl)pyrazino[2',1':6,1] --
Line 41, "-6-3.4-methylenedioxyphenyl)-" should
be -- -6-(3,4-methylenedioxyphenyl) --

Column 43,
Line 4, "N,8.91S,6.8;" should be -- N, 8.91; S,6.8; --
Line 35, "[1.4]" should be -- [1,4] --
Line 49, "[2',1':6.1]" should be -- [2',1':6,1] -

Column 44,
Line 3, "9614." should be -- 96/4. --
Line 13, "[3,4b]" should be -- [3,4-b] --
Lines 46 and 62, "9812." should be -- 98/2. --

Column 45,
Lines 43-44, "-6-3,4-hydroxyphenyl)" should be
-- -6-(3,4-dihydroxyphenyl) --
Lines 61-62, "[3,4b]" should be -- [3,4-b] --
Line 66, "92/810.1%" should be -- 92/8/0.1% --
Line 67, "isopropanolpropyl" should be -- isopropanol/propyl --

Column 48,
Line 38, "177 503-522" should be -- 177, 503-522 --

UNITED STATES PATENT AND TRADEMARK OFFICE
CERTIFICATE OF CORRECTION

PATENT NO. : 6,127,542
DATED : October 3, 2000
INVENTOR(S) : Daugan

It is certified that error appears in the above-identified patent and that said Letters Patent is hereby corrected as shown below:

<u>Column 49,</u>
Lines 23-37, the two tables in Example 122 should be one table.

Signed and Sealed this

Twenty-fourth Day of August, 2004

JON W. DUDAS
*Director of the United States Patent and Trademark Office*